United States Patent
Ogihara et al.

(10) Patent No.: US 12,076,171 B2
(45) Date of Patent: Sep. 3, 2024

(54) COVER FOR BLOOD PRESSURE METER, AND BLOOD PRESSURE METER

(71) Applicant: OMRON HEALTHCARE Co., Ltd., Muko (JP)

(72) Inventors: Tsuyoshi Ogihara, Kyoto (JP); Yoshikazu Inami, Kyoto (JP); So Noguchi, Osaka (JP); Shuji Tsuruta, Osaka (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 1329 days.

(21) Appl. No.: 16/683,484

(22) Filed: Nov. 14, 2019

(65) Prior Publication Data
US 2020/0078124 A1   Mar. 12, 2020

Related U.S. Application Data

(63) Continuation of application No. PCT/JP2018/021004, filed on May 31, 2018.

(30) Foreign Application Priority Data

Jul. 11, 2017   (JP) .................................. 2017-135546

(51) Int. Cl.
*A61B 50/00* (2016.01)
*A45C 13/02* (2006.01)
(Continued)

(52) U.S. Cl.
CPC .............. *A61B 50/00* (2016.02); *A45C 13/02* (2013.01); *A61B 5/02141* (2013.01);
(Continued)

(58) Field of Classification Search
CPC . A45C 2013/025; A45C 13/002; A45C 13/02; A61B 50/00; A61B 5/02141;
(Continued)

(56) References Cited

U.S. PATENT DOCUMENTS

| | | | | |
|---|---|---|---|---|
| 7,122,009 B2* | 10/2006 | Fumuro | ............. | A61B 5/02141 600/490 |
| 8,434,601 B2* | 5/2013 | Hou | ....................... | A45C 13/02 248/455 |
| 2011/0036473 A1* | 2/2011 | Chan | ..................... | A45C 13/02 150/113 |

FOREIGN PATENT DOCUMENTS

| | | |
|---|---|---|
| JP | H03-97443 A | 4/1991 |
| JP | H05-18502 U | 3/1993 |

(Continued)

OTHER PUBLICATIONS

Jul. 17, 2018 Search Report issued in International Patent Application No. PCT/JP2018/021004.

*Primary Examiner* — David J. McCrosky
(74) *Attorney, Agent, or Firm* — Oliff PLC

(57) ABSTRACT

In the cover for a blood pressure meter according to the invention, a coupling region that is detachably attached to a bottom surface of a main body is provided on one end. A tray region that is disposed so as to face a back surface of the main body and receives an accommodated cuff belt is connected to the coupling region. A panel cover region capable of covering a front panel of the main body is provided on the other end. A storage cover region that connects the tray region and the panel cover region is provided. In a cover-coupled state where the coupling region is detachably attached to the bottom surface of the main body, the panel cover region and the storage cover region are configured to be openable and closable with respect to the front panel and the tray region.

13 Claims, 22 Drawing Sheets

(51) Int. Cl.
*A61B 5/021* (2006.01)
*A61B 5/022* (2006.01)

(52) U.S. Cl.
CPC .......... *A61B 5/022* (2013.01); *A61B 5/02233* (2013.01); *A61B 2050/0053* (2016.02); *A61B 2050/0056* (2016.02); *A61B 2050/0079* (2016.02); *A61B 2050/008* (2016.02); *A61B 2050/0085* (2016.02); *A61B 2562/247* (2013.01)

(58) Field of Classification Search
CPC ........ A61B 5/02233; A61B 2050/0053; A61B 2050/0079; A61B 2562/247; A61B 2050/005; A61B 2050/0067; A61B 2050/0068; A61B 2050/007; A61B 2050/0074; A61B 2050/0085
See application file for complete search history.

(56) References Cited

FOREIGN PATENT DOCUMENTS

| | | |
|---|---|---|
| JP | H08-107885 A | 4/1996 |
| JP | 2002-45339 A | 2/2002 |
| JP | 2010-75342 A | 4/2010 |

* cited by examiner

COVER FOR BLOOD PRESSURE METER, AND BLOOD PRESSURE METER

CROSS-REFERENCE TO RELATED APPLICATION

This is a continuation application of International Application No. PCT/JP2018/021004, with an International filing date of May 31, 2018, which claims priority of Japanese Patent Application No. 2017-135546 filed on Jul. 11, 2017, the entire content of which is hereby incorporated by reference.

TECHNICAL FIELD

The present invention relates to a cover for a blood pressure meter, and more particularly to a cover for a blood pressure meter that can accommodate a cuff belt.

The present invention also relates to a blood pressure meter having such a cover for a blood pressure meter.

BACKGROUND ART

Conventionally, as a blood pressure meter having this type of cover for a blood pressure meter, there has been known a structure in which a substantially plate-like cover capable of covering an upper surface (front panel) of a main body of the blood pressure meter is attached to the back side (back surface) of the main body through a hinge, as disclosed in Patent Document 1 (JP 2010-75342 A), for example. In this blood pressure meter, a cuff belt rolled into a roll shape is accommodated in a cuff-belt storage recess surrounded by the back surface of the main body and a base portion of the cover.

SUMMARY OF THE INVENTION

However, in the above blood pressure meter, the cover is attached to the main body of the blood pressure meter with the hinge, and the cover cannot be removed from the main body. For this reason, there has been a problem that the blood pressure meter becomes bulky because of the cover.

Hence, an object of the present invention is to provide a cover for a blood pressure meter that can accommodate a cuff belt, and is removable from a main body of the blood pressure meter.

Another object of the invention is to prove a blood pressure meter from which such a cover for a blood pressure meter can be removed, and can be used in a small size.

In order to solve the problem described above, a cover for a blood pressure meter capable of accommodating a cuff belt of the present disclosure includes:

a main body of a blood pressure meter having a bottom surface placed on a support surface, a front panel extending so that its height gradually increases from the front toward the rear or extending horizontally, and a back surface extending in a height direction by connecting a rear edge portion of the bottom surface and a rear edge portion of the front panel, the cover for a blood pressure meter having a belt-like outer shape extending from one end to another end along a longitudinal direction, the cover for a blood pressure meter comprising:

a coupling region provided on the one end side in the longitudinal direction and detachably attached to the bottom surface of the main body;

a tray region connected to a side of the coupling region opposite to the one end, disposed so as to face the back surface of the main body, and receiving the accommodated cuff belt;

a panel cover region provided on the other end side in the longitudinal direction and capable of covering the front panel of the main body; and a storage cover region connecting the tray region and the panel cover region, wherein in a cover-coupled state where the coupling region is detachably attached to the bottom surface of the main body, the panel cover region and the storage cover region are configured to be openable and closable with respect to the front panel and the tray region.

In this specification, the "main body" of the blood pressure meter refers to a casing and includes at least a bottom surface, a front panel, and a back surface. Typically, the front panel is provided with an operation portion for a user to instruct on/off of blood pressure measurement, and a display that displays information on blood pressure.

Additionally, the "support surface" typically refers to a horizontal surface such as a desk, a table, or a floor. Note, however, that the support surface may be slightly inclined with respect to a horizontal plane.

Additionally, the panel cover region and the storage cover region capable of being "opened" with respect to the front panel and the tray region means that the panel cover region and the storage cover region can be separated from the front panel and the tray region, and the front panel and the tray region can become accessible by the user. The panel cover region and the storage cover region capable of being "closed" with respect to the front panel and the tray region means that the panel cover region and the storage cover region can come close to the front panel and the tray region, and cover the front panel and the tray region.

In another aspect, the blood pressure meter of the present disclosure comprises a removable cover for a blood pressure meter capable of accommodating a cuff belt, wherein:

a main body of the blood pressure meter has a bottom surface placed on a support surface, a front panel extending so that its height gradually increases from the front toward the rear or extending horizontally, and a back surface extending in a height direction by connecting a rear edge portion of the bottom surface and a rear edge portion of the front panel;

the cover for a blood pressure meter has a belt-like outer shape extending from one end to another end along a longitudinal direction, and includes a coupling region provided on the one end side in the longitudinal direction and detachably attached to the bottom surface of the main body, a tray region connected to a side of the coupling region opposite to the one end, facing the back surface of the main body, and receiving the accommodated cuff belt, a panel cover region provided on the other end side in the longitudinal direction and capable of covering the front panel of the main body, and a storage cover region connecting the tray region and the panel cover region; and in a cover-coupled state where the coupling region is detachably attached to the bottom surface of the main body, the panel cover region and the storage cover region are configured to be openable and closable with respect to the front panel and the tray region.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, embodiments of the invention will be described in detail with reference to the drawings.

Figure 1:
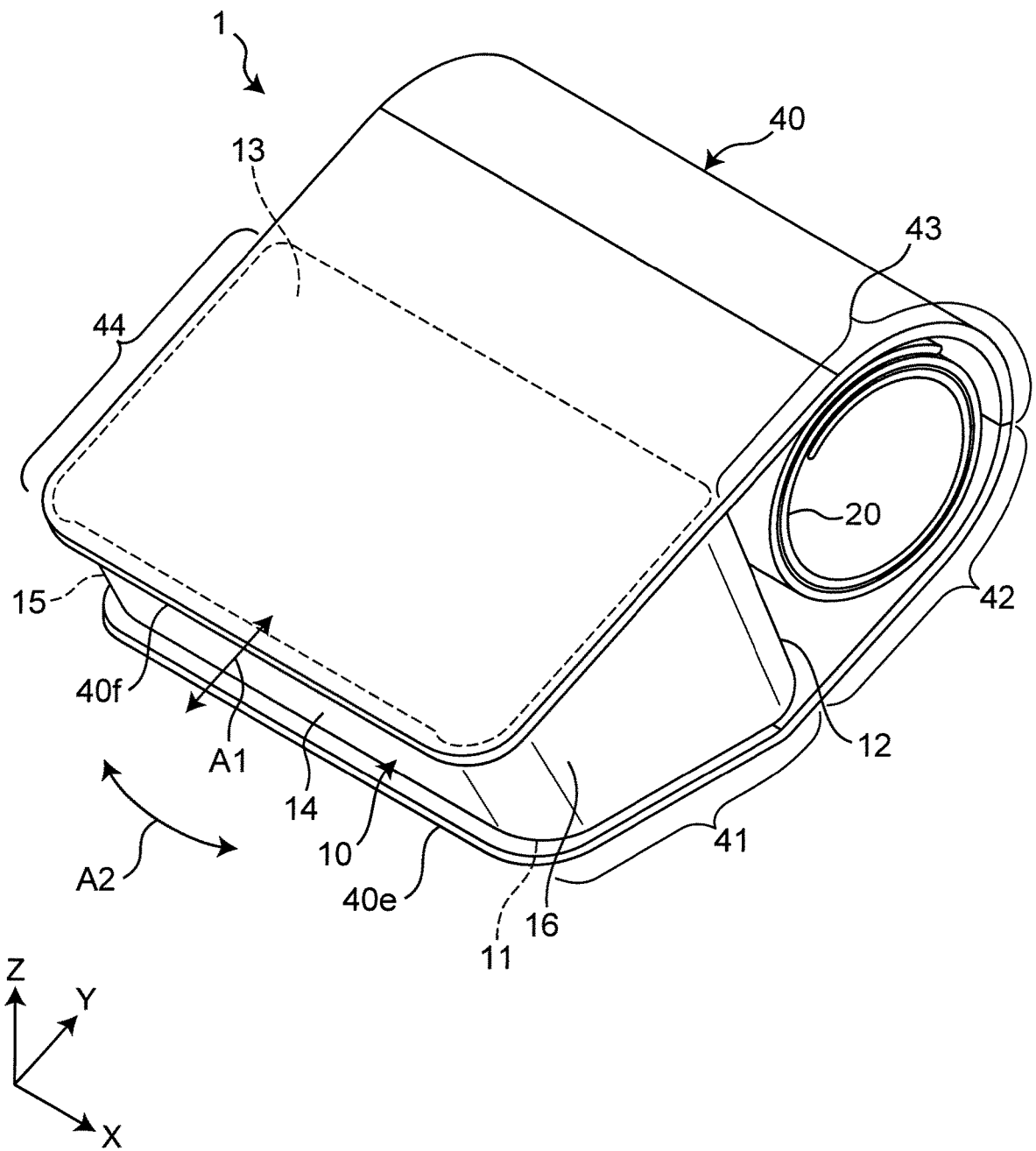
FIG. 1 is a perspective view showing an appearance of a blood pressure meter covered with a cover for a blood pressure meter according to an embodiment of the invention.

FIG. 1 shows an appearance of a blood pressure meter (the whole blood pressure meter is indicated by reference numeral 1) covered with a cover for a blood pressure meter 40 according to one embodiment of the invention as viewed obliquely. FIG. 3 shows an appearance of the blood pressure meter 1 in a state where the cover for a blood pressure meter 40 is open. Additionally, FIGS. 2A and 2B show the blood pressure meter 1 of FIG. 1 as viewed from the right side (+X side) and the front (−Y side), respectively.

In this example, a main body 10 that is a casing of the blood pressure meter 1 includes a bottom surface 11 placed on an XY plane (see FIG. 1) as a support surface, a front panel 13, a back surface 12, a front surface 14, a left side surface 15, and a right side surface 16. Note that in this example, the XY plane as the support surface represents a horizontal plane such as a desk, a table, or a floor. Note, however, that the support surface may be slightly inclined with respect to a horizontal plane. The height direction perpendicular to the XY plane is represented by an Z-axis.

Figure 2A:
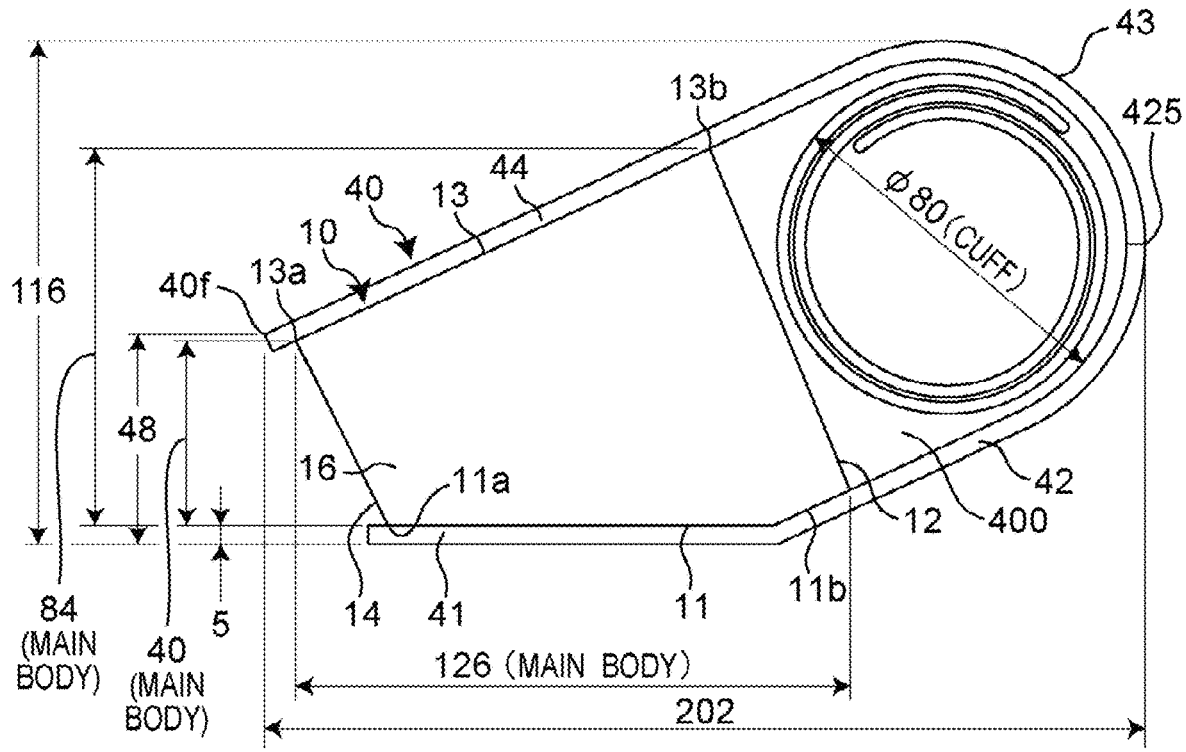
FIG. 2A is a diagram showing the blood pressure meter of FIG. 1 as viewed from the right side (+X side).
Figure 2B:
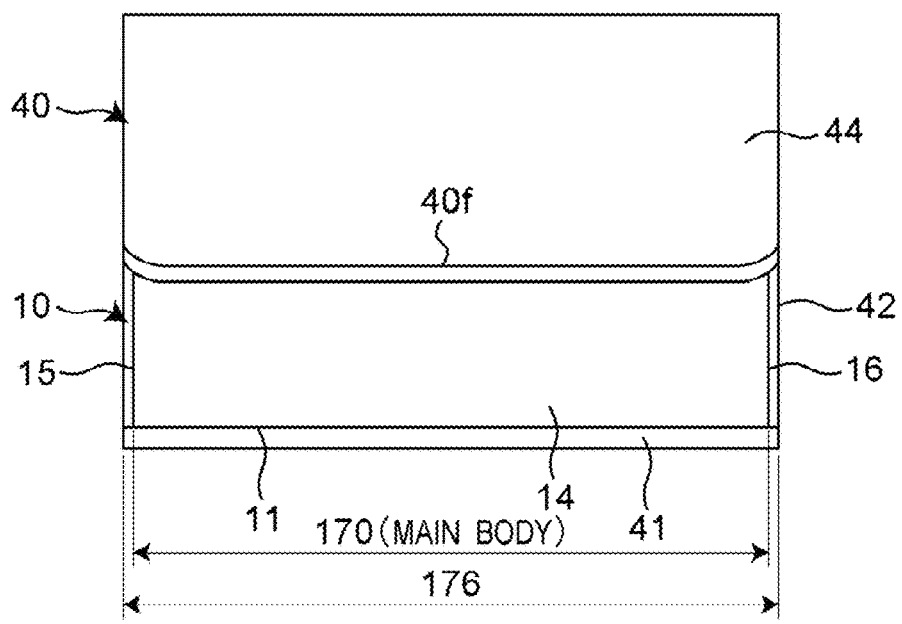
FIG. 2B is a diagram showing the blood pressure meter of FIG. 1 as viewed from the front (−Y side).
Figure 3:
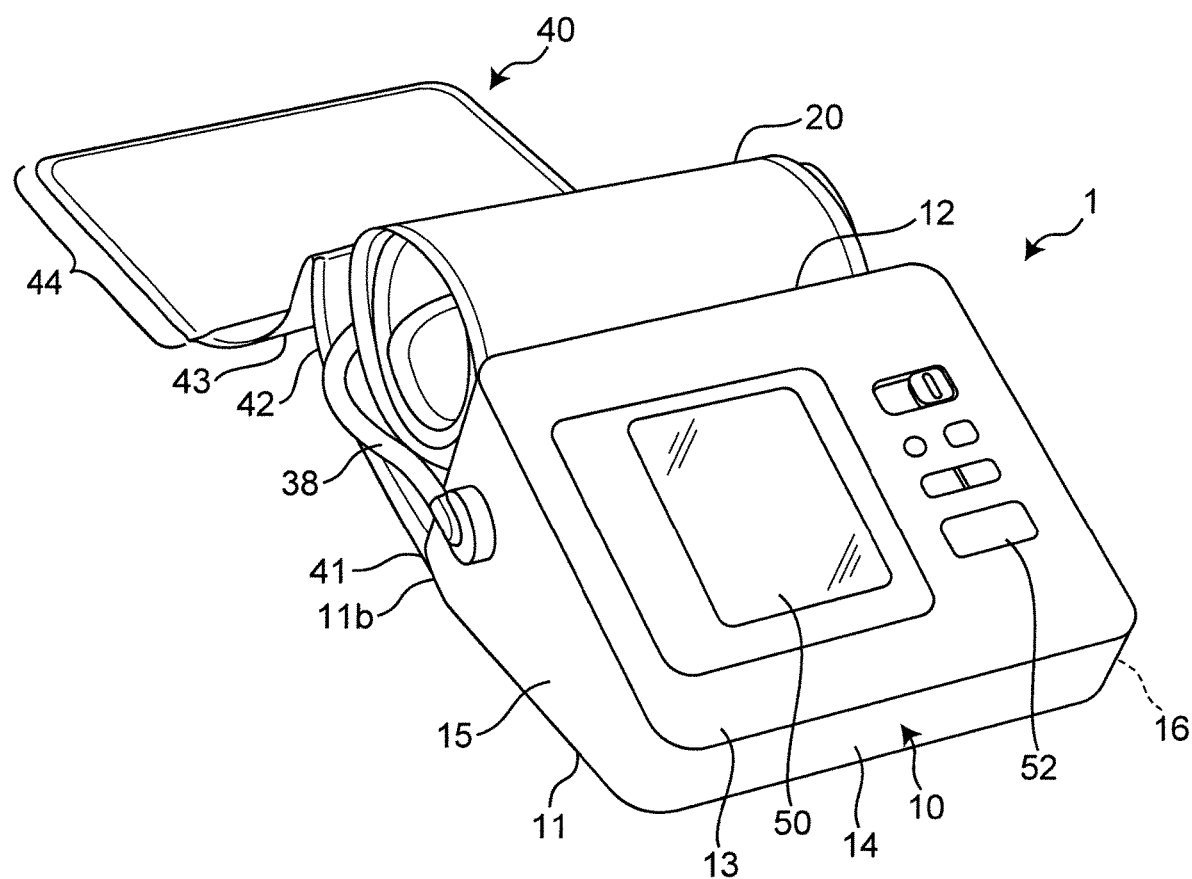
FIG. 3 is a perspective view showing an appearance of the blood pressure meter in a state where the cover for a blood pressure meter is opened.

As can be seen from FIG. 2A, the front panel 13 is an inclined surface extending at an angle of about 25 degrees with respect to the horizontal plane, so that its height gradually increases from the front toward the rear (+Y direction). While the bottom surface 11 is substantially flat, a rear edge portion 11b of the bottom surface 11 is an inclined surface inclined by about 25 degrees with respect to the horizontal plane, so that its height gradually increases from the front toward the rear (+Y direction). The front surface 14 extends in the height direction by connecting a front edge portion 11a of the bottom surface 11 and a front edge portion 13a of the front panel 13. The back surface 12 extends in the height direction by connecting the rear edge portion 11b of the bottom surface 11 and a rear edge portion 13b of the front panel 13. The front surface 14 and the back surface 12 are inclined surfaces inclined by about 30 degrees and about 20 degrees, respectively, with respect to the vertical surface, so as to be inclined frontward from the bottom toward the top (+Z direction).

As can be seen from FIG. 3, in this example, the front panel 13 is provided with an operation portion 52 for the user to instruct on/off of blood pressure measurement, and a display 50 that displays information on blood pressure (maximum blood pressure, minimum blood pressure, pulse rate, and the like).

Additionally, a cuff belt 20 is attached to a left side surface 15 of the main body 10 through a flexible elongated air tube 38. The cuff belt 20 is used to squeeze a part to be measured by being wound around the upper arm as the part to be measured in this example when measuring blood pressure. When not measuring blood pressure, the cuff belt 20 is rolled and stored in the form of a roll shape having an outer diameter of about 80 mm (the assumed minimum outer diameter is 60 mm and the maximum outer diameter is 95 mm) in this example.

Figure 4:
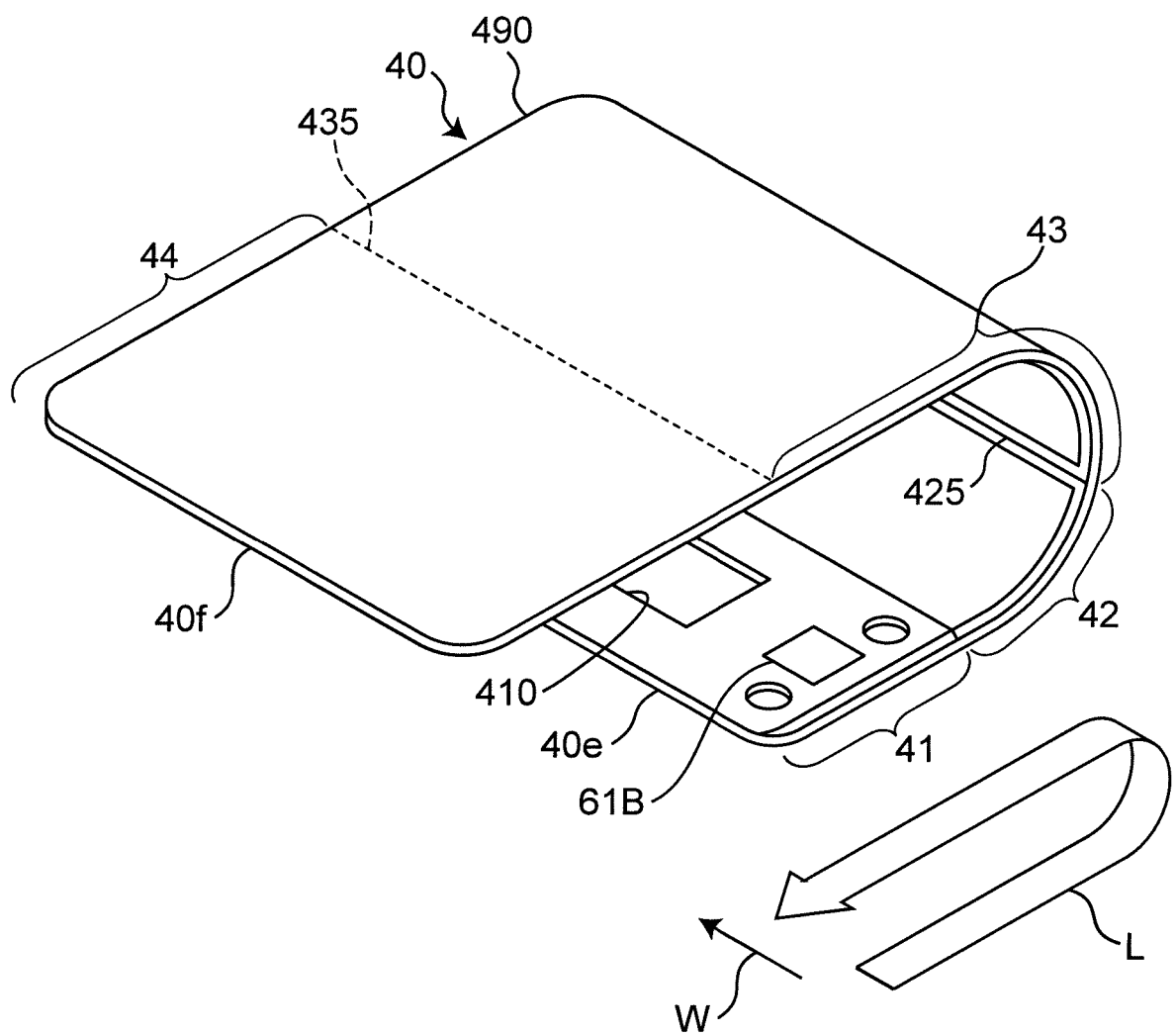
FIG. 4 is a diagram showing the cover for a blood pressure meter alone as viewed from an angle corresponding to FIG. 1.

FIG. 4 shows the cover for a blood pressure meter 40 removed from the main body 10 as viewed at an angle corresponding to FIG. 1. The cover for a blood pressure meter 40 has a belt-like outer shape 490 extending along a longitudinal direction L from one end 40e to the other end 40f.

Figure 6:
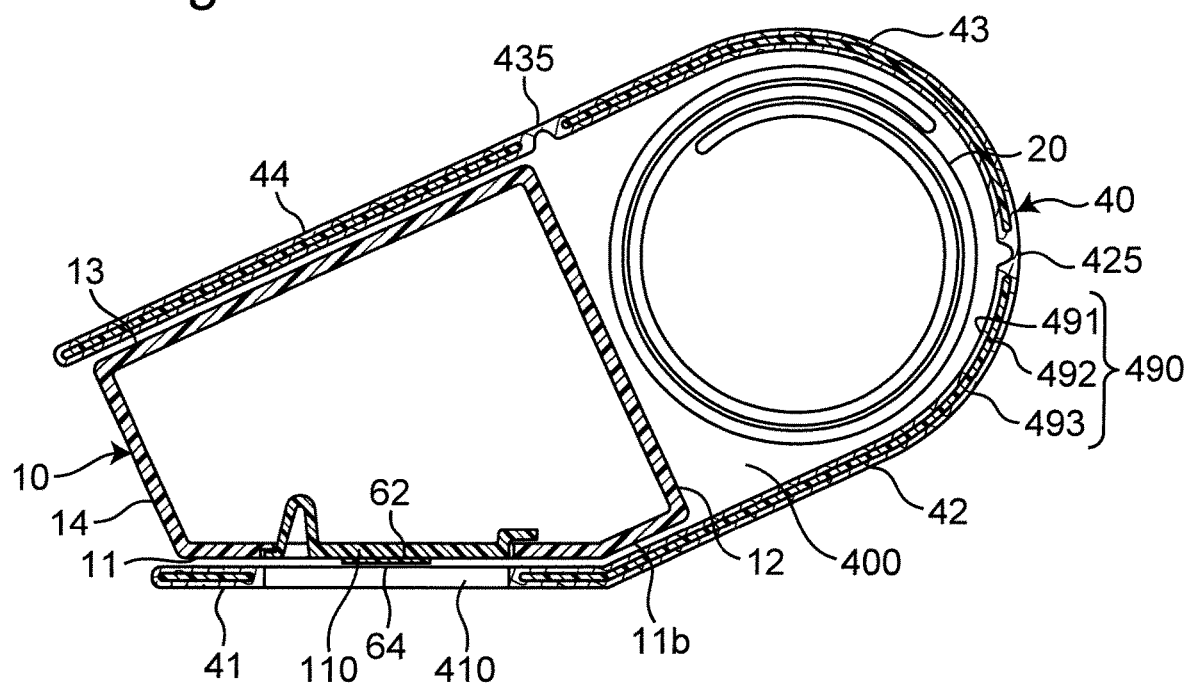
FIG. 6 is a cross-sectional view of the blood pressure meter of FIG. 1 as viewed from the right side.

As shown in FIG. 6 (a cross-sectional view of blood pressure meter 1 of FIG. 1 as viewed from right side), the belt-like outer shape 490 is configured of an inner cloth 491 facing the main body 10, an outer cloth 493 facing the inner cloth 491, and a plate-like core material 492 sandwiched between the inner cloth 491 and the outer cloth 493. The sizes of the inner cloth 491 and the outer cloth 493 are set slightly larger than the size (total size) of the plate-like core material 492. In this example, an outer peripheral edge of the inner cloth 491 and an outer peripheral edge of the outer cloth 493 are brought into contact with each other and sewn, so that the plate-like core material 492 is included between the inner cloth 491 and the outer cloth 493.

In this example, both the inner cloth 491 and the outer cloth 493 are made of suede leather having a thickness of 1.5 mm. Additionally, the core material 492 is made of polypropylene (PP) having a thickness of 2 mm.

As shown in FIG. 4, the cover for a blood pressure meter 40 includes a coupling region 41, a tray region 42, a storage cover region 43, and a panel cover region 44 from the one end 40e side to the other end 40f side in the longitudinal direction L in this order. The coupling region 41 provided on the one end 40e side is a region that is detachably attached to the bottom surface 11 of the main body 10. The tray region 42 is a region that is connected to the side of the coupling region 41 opposite to the one end 40e, is disposed so as to face the back surface 12 of the main body 10, and receives the stored cuff belt 20. The panel cover region 44 is a region that is provided on the other end 40f side and can cover the front panel 13 of the main body 10. The storage cover region 43 is a region that connects the tray region 42 and the panel cover region 44.

As shown in FIG. 6, in a first boundary portion 425 that connects the tray region 42 and the storage cover region 43, a gap is formed between the core material 492 forming the storage cover region 43 and the core material 492 forming the tray region 42 in the longitudinal direction L. As a result, the first boundary portion 425 is formed only of the inner cloth 491 and the outer cloth 493, and is configured to be soft enough to bend by the weight of the storage cover region 43. In this way, the first boundary portion 425 that connects the tray region 42 and the storage cover region 43 is configured to be foldable. Similarly, in a second boundary portion 435 that connects the storage cover region 43 and the panel cover region 44, a gap is formed between the core material 492 forming the storage cover region 43 and the core material 492 forming the panel cover region 44 in the longitudinal direction L. As a result, the panel cover region 44 is configured to be foldable with respect to the storage cover region 43. Note that in the first and second boundary portions 425 and 435, the inner cloth 491 and the outer cloth 493 are in contact with each other and sewn. Accordingly, the core material 492 does not move across the first and second boundary portions 425 and 435 in the longitudinal direction L inside the cover for a blood pressure meter 40.

The shapes of the coupling region 41 and the panel cover region 44 are generally flat according to the shape of the core material 492 forming them. In the state shown in FIG. 6 (cover-coupled state), the tray region 42 maintains its shape curving so as to protrude downward and extending obliquely upward from the rear edge portion 11b of the bottom surface 11 of the main body 10, according to the shape of the core material 492 forming the tray region 42. Accordingly, the tray region 42 is suitable for receiving the cuff belt 20 rolled into a roll shape. The storage cover region 43 curves so as to protrude outward (in a direction headed toward the outer cloth 493 from the inner cloth 491) when viewed from the side as shown in FIG. 6, according to the shape of the core material 492 forming the storage cover region 43.

Figure 5:
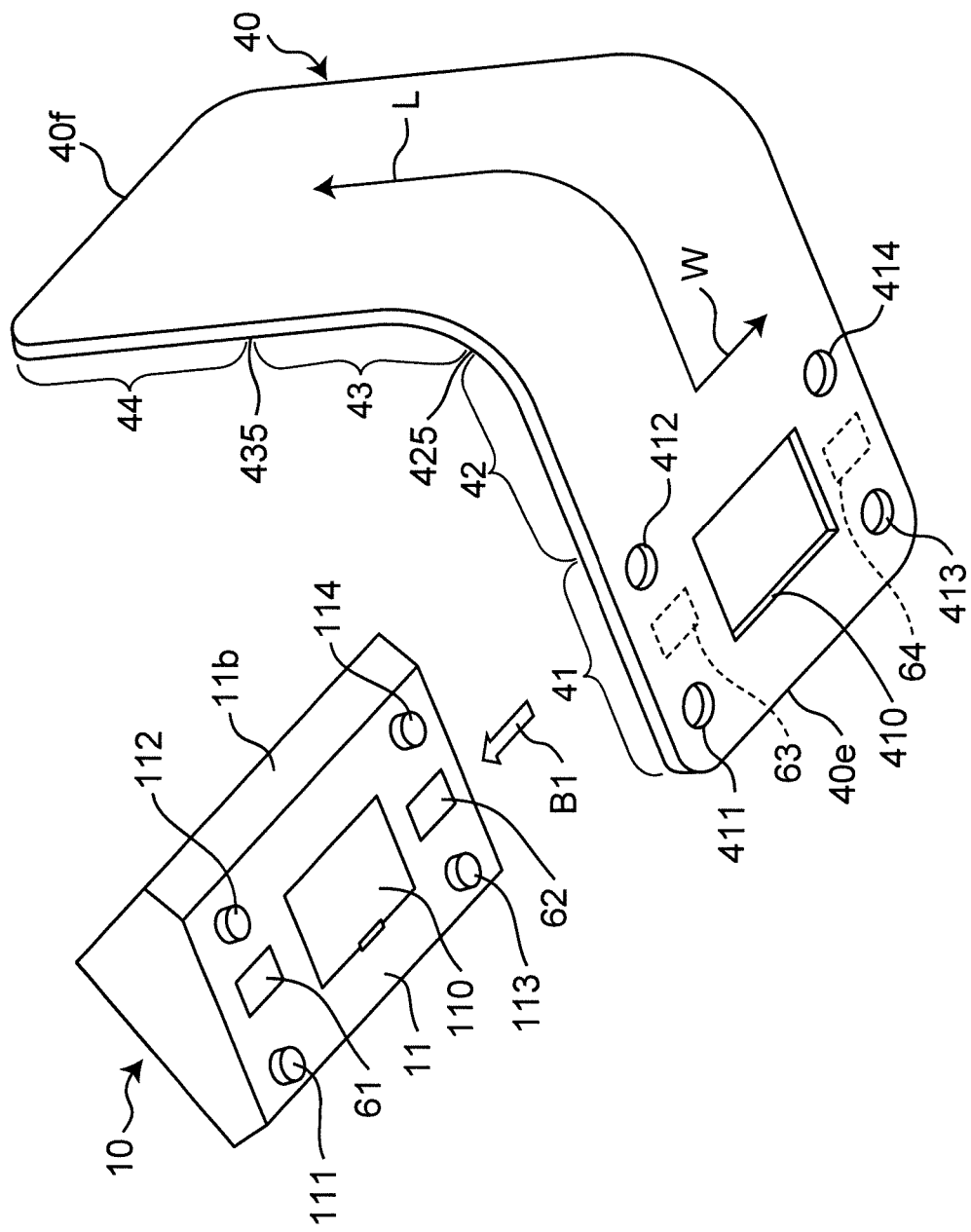
FIG. 5 is a diagram showing a detailed configuration of a coupling region between a bottom surface of a main body of the blood pressure meter and the cover for a blood pressure meter.

As shown in FIG. 5, in this example, the bottom surface 11 of the main body 10 is provided with a substantially rectangular battery lid 110 at the substantial center, and short cylindrical rubber legs 111, 112, 113, and 114 at the four corners. In a state where the battery lid 110 is removed from the main body 10, it is possible to insert a battery into a battery storage portion (not shown) built in the main body 10 from the outside, or to remove it. In a state where the battery lid 110 is attached to the main body 10, the battery lid 110 prevents the battery accommodated in the battery storage portion from dropping off from the main body 10. The rubber legs 111, 112, 113, and 114 maintain the posture of the main body 10 when the main body 10 is placed on the XY plane (see FIG. 1). Additionally, of the bottom surface 11 of the main body 10 shown in FIG. 5, regions corresponding to both sides in the width direction of the battery lid 110 (direction X shown in FIG. 1) are provided with rectangular first hook-and-loop fasteners 61 and 62 in this example. In this example, the first hook-and-loop fasteners 61 and 62 are configured by providing multiple visually minute loops in a standing manner on a planar base material.

On the other hand, in the coupling region 41 of the cover for a blood pressure meter 40, a substantially rectangular opening 410 is provided at the substantial center, and circular through holes 411, 412, 413, and 414 are provided at the four corners. The opening 410 is disposed in a position corresponding to the battery lid 110 of the main body 10. As a result, even in a state where the coupling region 41 is attached to the bottom surface 11 of the main body 10 (cover-coupled state), it is possible to remove the battery lid 110 from the main body 10 or attach the battery lid 110 to the main body 10. Additionally, the through holes 411, 412, 413, and 414 are disposed in positions corresponding to the rubber legs 111, 112, 113, and 114 of the main body 10. As a result, the rubber legs 111, 112, 113, and 114 are fitted into the through holes 411, 412, 413, and 414, respectively, in the cover-coupled state, and as a result, the inner cloth 491 of the coupling region 41 is brought into tight contact with the bottom surface 11 of the main body 10. Additionally, of the coupling region 41 (the inner cloth 491 side) of the cover for a blood pressure meter 40, regions corresponding to both sides in a width direction W of the opening 410 are provided with rectangular second hook-and-loop fasteners 63 and 64. In this example, the second hook-and-loop fasteners 63 and 64 are configured by providing multiple visually minute hooks in a standing manner on a planar base material. When attaching the cover for a blood pressure meter 40 to the main body 10, the user aligns the through holes 411, 412, 413, and 414 provided in the coupling region 41 of the cover for a blood pressure meter 40 with the rubber legs 111, 112, 113, and 114 provided on the bottom surface 11 of the main body 10, and brings the inner cloth 491 of the coupling region 41 into contact with the bottom surface 11 of the main body 10 as indicated by arrow B1 in FIG. 5. As a result, the position of the opening 410 is aligned with the battery lid 110, and the positions of the second hook-and-loop fasteners 63 and 64 are aligned with the first hook-and-loop fasteners 61 and 62. Accordingly, the second hook-and-loop fasteners 63 and 64 are detachably engaged with the first hook-and-loop fasteners 61 and 62 to form the cover-coupled state. In this way, the coupling region 41 is easily attached to the bottom surface 11 of the main body 10. Conversely, when removing the cover for a blood pressure meter 40, the user pulls the bottom surface 11 of the main body 10 and the coupling region 41 away from each other. Then, the second hook-and-loop fasteners 63 and 64 are peeled off from the first hook-and-loop fasteners 61 and 62, and the coupling region 41 is easily removed from the bottom surface 11 of the main body 10. This forms a cover non-coupled state in which the cover for a blood pressure meter 40 is not attached to the main body 10. In this cover non-coupled state, the blood pressure meter 1 does not become bulky because of the cover for a blood pressure meter 40. Hence, the user can use the blood pressure meter 1 in a small size.

In the above-described cover-coupled state, the tray region 42 continuous with the coupling region 41 is disposed so as to face the back surface 12 of the main body 10, as shown in FIG. 6. Moreover, in FIG. 6, the main body 10 of the blood pressure meter 1 is covered with the cover for a blood pressure meter 40. That is, the panel cover region 44 and the storage cover region 43 are closed with respect to the front panel 13 and the tray region 42.

Figure 7:
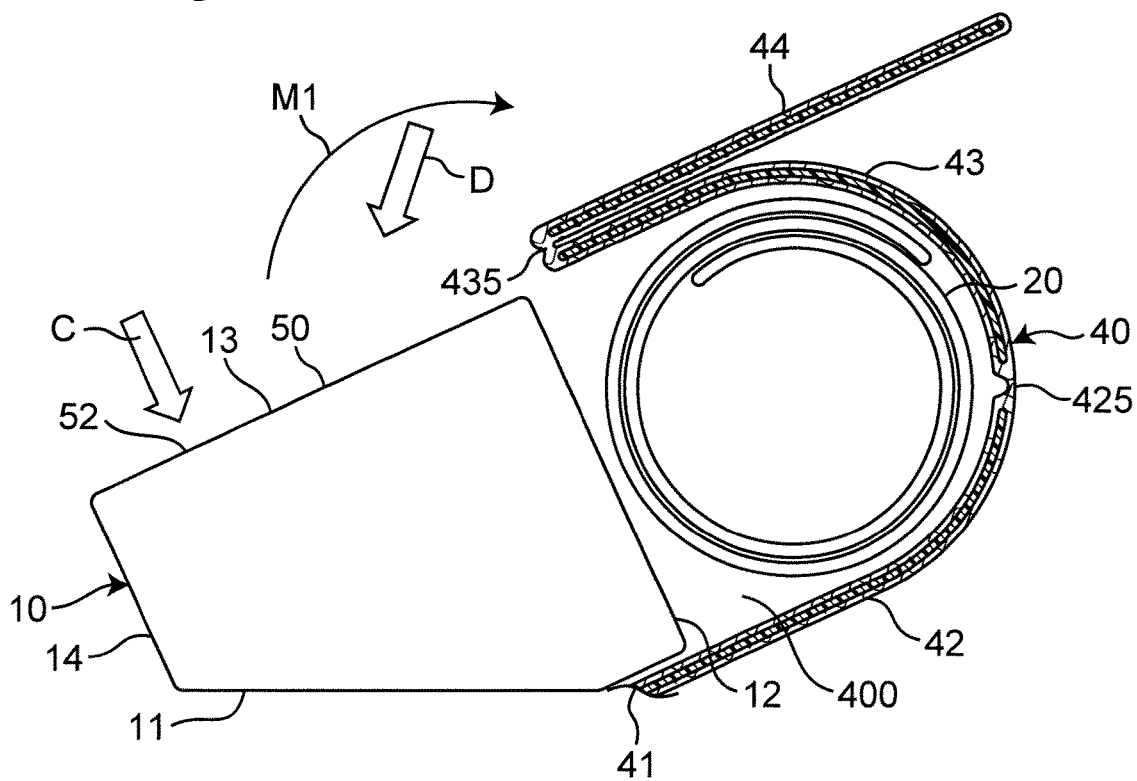
FIG. 7 is a diagram showing a state in which a panel cover region is being opened with respect to a front panel while a storage cover region covers a tray region in a cover-coupled state of the blood pressure meter.

Here, as described above, the second boundary portion 435 connecting the panel cover region 44 and the storage cover region 43 is configured to be foldable. Hence, as shown in FIG. 7, in the cover-coupled state, while the storage cover region 43 covers the tray region 42, the panel cover region 44 can be opened in a direction indicated by arrow M1 with respect to the front panel 13, or be closed in the opposite direction. Accordingly, by opening the panel cover region 44 with respect to the front panel 13 while the storage cover region 43 covers the tray region 42, for example, the panel cover region 44 is separated from the front panel 13, and the front panel 13 becomes accessible by the user as indicated by arrow C. For example, the user can operate the operation portion 52 provided on the front panel 13 to instruct on/off of blood pressure measurement. Additionally, the user can obtain information related to blood pressure (e.g., a blood pressure value obtained as a measurement result) by looking at the display 50 provided on the front panel 13.

Figure 8:
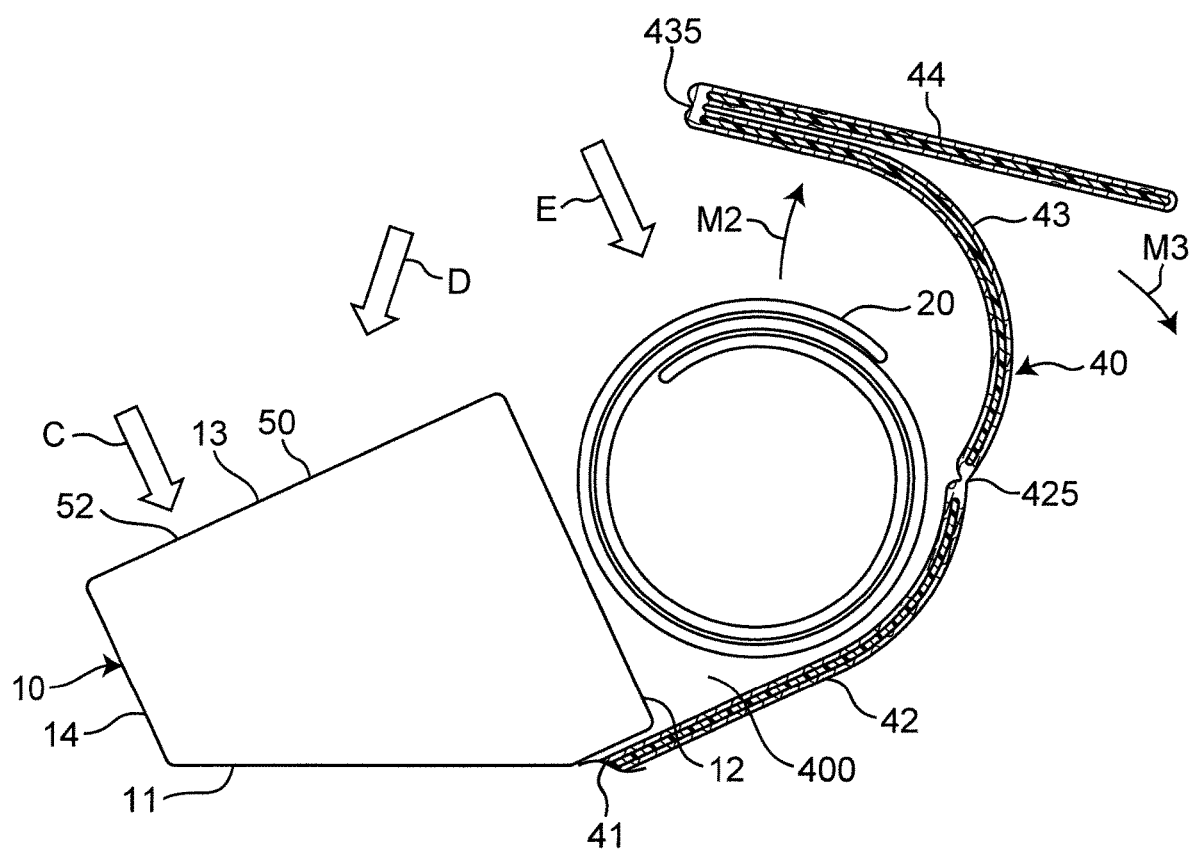
FIG. 8 is a diagram showing a state in which the panel cover region and the storage cover region are opened with respect to the front panel and the tray region in the cover-coupled state of the blood pressure meter.

Furthermore, the first boundary portion 425 that connects the storage cover region 43 and the tray region 42 is configured to be foldable. Hence, as shown in FIG. 8, in the cover-coupled state, the panel cover region 44 and the storage cover region 43 can be opened in directions indicated by arrows M2 and M3 with respect to the front panel 13 and the tray region 42, or be closed in directions opposite thereto.

For example, when the panel cover region 44 and the storage cover region 43 are opened with respect to the front panel 13 and the tray region 42, the panel cover region 44 and the storage cover region 43 are separated from the front panel 13 and the tray region 42, and the front panel 13 and the tray region 42 become accessible by the user. For example, as indicated by arrow C in FIG. 8 as in FIG. 7, the user can operate the operation portion 52 provided on the front panel 13 to instruct on/off of blood pressure measurement. Additionally, the user can obtain information related to blood pressure (e.g., a blood pressure value obtained as a measurement result) by looking at the display 50 provided on the front panel 13. Further, when the blood pressure measurement is completed, for example, the user can place the cuff belt 20 rolled into a roll shape, for example, in a space 400 where the back surface 12 of the main body 10 and the tray region 42 face each other as indicated by arrow E. As a result, the placed cuff belt 20 is received by the back surface 12 of the main body 10 and the tray region 42. Additionally, when starting blood pressure measurement, the user can take out the cuff belt 20 from the space 400 where the back surface 12 of the main body 10 and the tray region 42 face each other in a direction opposite to arrow E.

Additionally, since the first boundary portion 425 connecting the storage cover region 43 and the tray region 42 and the second boundary portion 435 connecting the panel cover region 44 and the storage cover region 43 are foldable, when the panel cover region 44 is opened with respect to the front panel 13, the panel cover region 44 and the storage cover region 43 do not maintain an upright state, and are laid down by their own weight as shown in FIG. 3. Hence, when viewed by the user from the back surface 12 side of the main body 10 as indicated by arrow D in FIG. 8, a problem that the display 50 (provided on the front panel 13 of the main body 10) is hidden by the panel cover region 44 and is difficult to see does not occur. Additionally, when the user opens and closes the panel cover region 44 with respect to the front panel 13, it is not necessary to apply a strong force to the panel cover region 44 and the storage cover region 43. Hence, the first boundary portion 425 connecting the storage cover region 43 and the tray region 42 and the second boundary portion 435 connecting the panel cover region 44 and the storage cover region 43 are less likely to break.

As shown in FIG. 6, when the panel cover region 44 and the storage cover region 43 are closed with respect to the front panel 13 and the tray region 42, the panel cover region 44 and the storage cover region 43 come close to the front panel 13 and the tray region 42, respectively, and cover the front panel 13 and the tray region 42. Thus, the main body 10 is covered and protected by the cover for a blood pressure meter 40. Additionally, when the cuff belt 20 (e.g., rolled into roll shape) is placed in a space where the back surface 12 of the main body 10 and the tray region 42 face each other, the cuff belt 20 is surrounded and held by the back surface 12 of the main body 10, the tray region 42, and the storage cover region 43. That is, a space in which the back surface 12 of the main body 10, the tray region 42, and the storage cover region 43 surround the cuff belt 20 (referred to as a "cuff belt storage portion" and indicated by same reference numeral as space 400 where the back surface 12 of the main body 10 and the tray region 42 face each other for purpose of simplification) is formed, and the cuff belt 20 is accommodated in the cuff belt storage portion 400.

As described above, the storage cover region 43 curves so as to protrude outward (in a direction headed toward the outer cloth 493 from the inner cloth 491) when viewed from the side as shown in FIG. 6, according to the shape of the core material 492 forming the storage cover region 43. Accordingly, even when the cuff belt 20 is not accommodated in the cuff belt storage portion 400, for example, the shape of the storage cover region 43 is not depressed downward and is maintained in an upwardly protruding state. Hence, the appearance is maintained.

Modification 1

Figure 9:
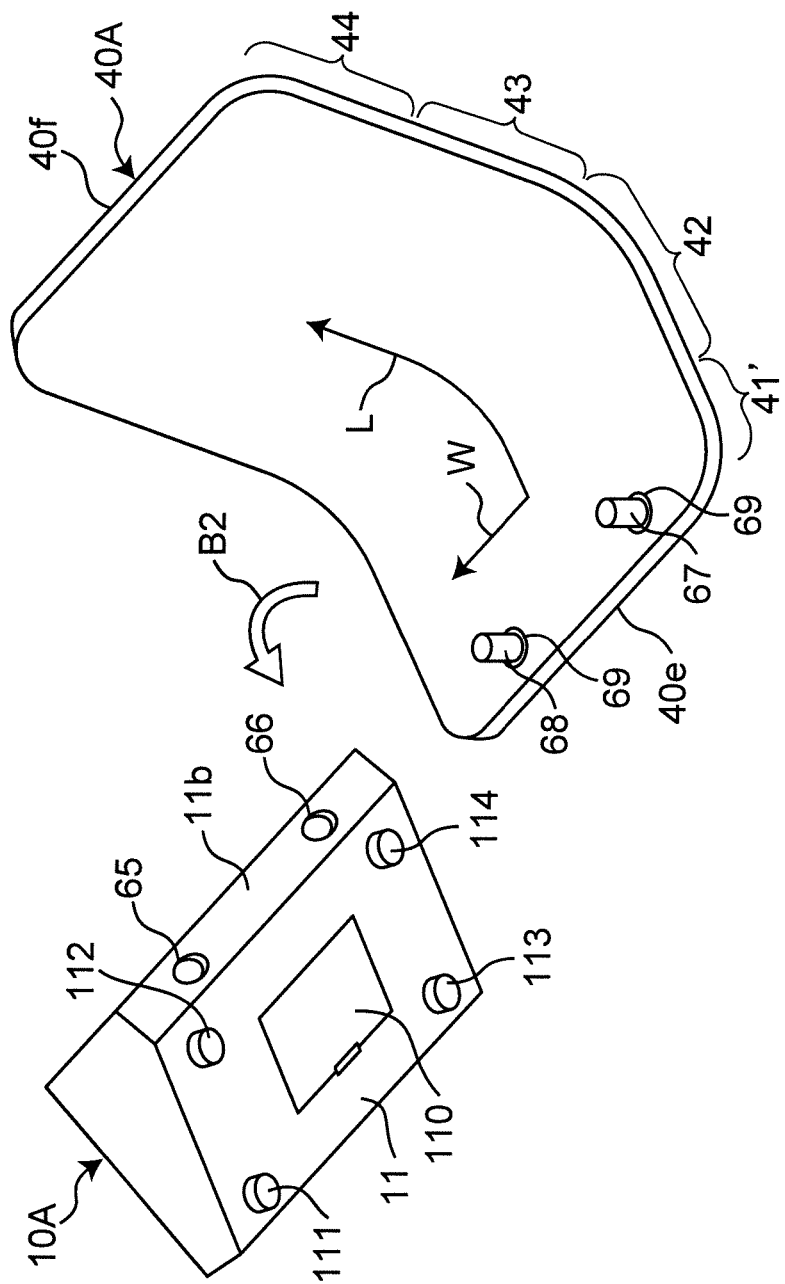
FIG. 9 is a diagram showing a modification of the structure in which the cover for a blood pressure meter is detachably attached to the main body.
Figure 10:
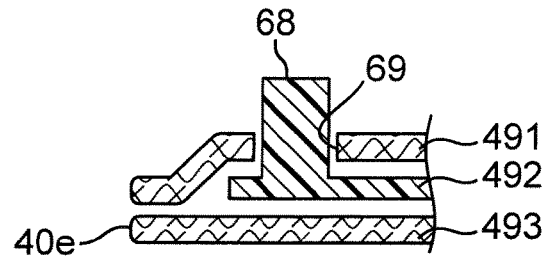
FIG. 10 is an enlarged cross-sectional view showing a configuration in the vicinity of a protrusion of the cover for a blood pressure meter of FIG. 9.
Figure 11:
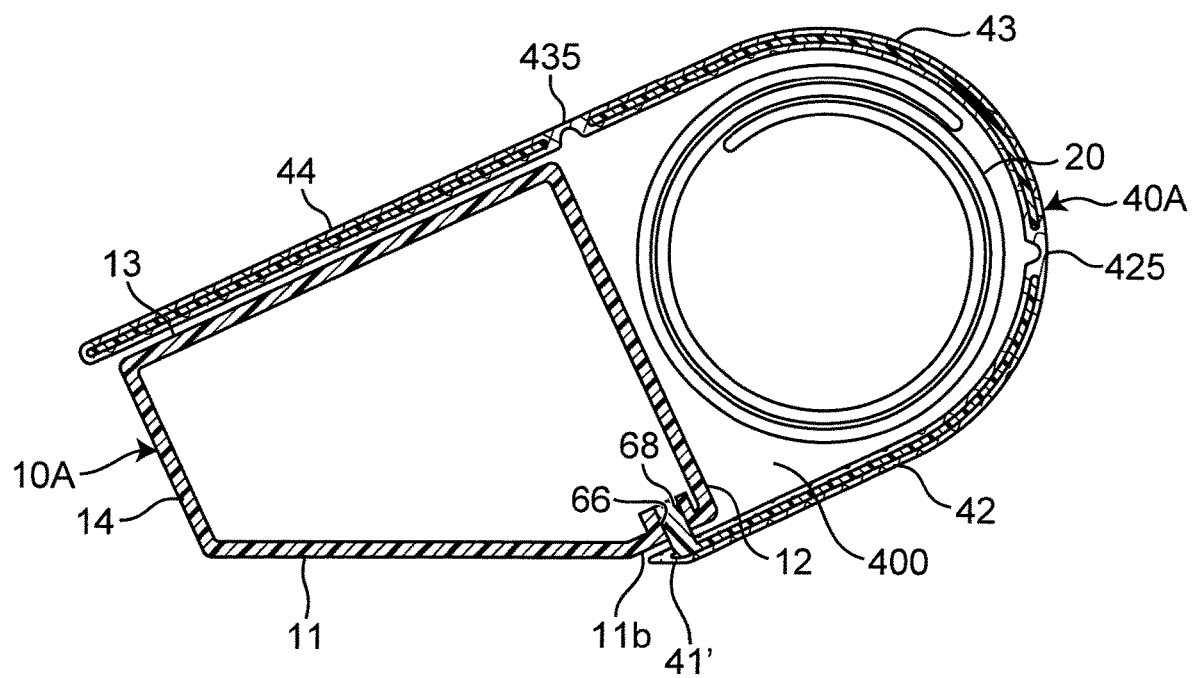
FIG. 11 is a cross-sectional view showing a state in which a cover for a blood pressure meter is attached to the main body of FIG. 9, and a panel cover region and a storage cover region are closed with respect to a front panel and a tray region.

FIGS. 9 to 11 show a modification of the structure in which the cover for a blood pressure meter 40 is detachably attached to the main body 10. In this example, the first hook-and-loop fasteners 61 and 62 and the second hook-and-loop fasteners 63 and 64 are omitted (the same applies to Modifications 2 and 3 described later).

In this example, as shown in FIG. 9, a main body (indicated by reference numeral 10A) has a pair of receiving holes 65 and 66 on both sides in the width direction (direction X shown in FIG. 1) on a rear edge portion 11b of the bottom surface 11. These receiving holes 65 and 66 are formed in a cylindrical shape. On the other hand, a cover for a blood pressure meter (indicated by reference numeral 40A) has cylindrical projections 67 and 68 dimensioned so as to closely fit into the receiving holes 65 and 66, respectively, in locations in a coupling region (indicated by reference numeral 41') corresponding to the receiving holes 65 and 66. These projections 67 and 68 are each formed integrally with a core material 492 as illustrated for the projection 68 in FIG. 10, and protrude to the outside through a through hole 69 provided in an inner cloth 491.

When attaching the cover for a blood pressure meter 40A, as indicated by arrow B2 in FIG. 9, the user aligns and closely fits the projections 67 and 68 provided in the coupling region 41' of the cover for a blood pressure meter 40A with the receiving holes 65 and 66 provided in the rear edge portion 11b of the bottom surface 11 of the main body 10A. FIG. 11 shows a state where the receiving hole 66 and the protrusion 68 are closely fitted (cover-coupled state). In this manner, the coupling region 41' is attached to the rear edge portion 11b of the bottom surface 11 of the main body 10A. Thus, the cover for a blood pressure meter 40A is easily attached to the main body 10A. Conversely, when removing the cover for a blood pressure meter 40A, the user pulls the bottom surface 11 of the main body 10A and the coupling region 41' away from each other. Then, the projections 67 and 68 are pulled out from the receiving holes 65 and 66 against frictional force, and the coupling region 41' is removed from the rear edge portion 11b of the bottom surface 11 of the main body 10A. Thus, the cover for a blood pressure meter 40A is easily removed from the main body 10A.

In this example, the coupling region 41' only needs to face the rear edge portion 11b of the bottom surface 11. Accordingly, the dimension in a longitudinal direction L of the coupling region 41' (hence the cover for a blood pressure meter 40A) can be reduced as compared with a case where the coupling region 41 faces substantially the entire area of the bottom surface 11. That is, the cover for a blood pressure meter 40A can be downsized.

Modification 2

Figure 12:
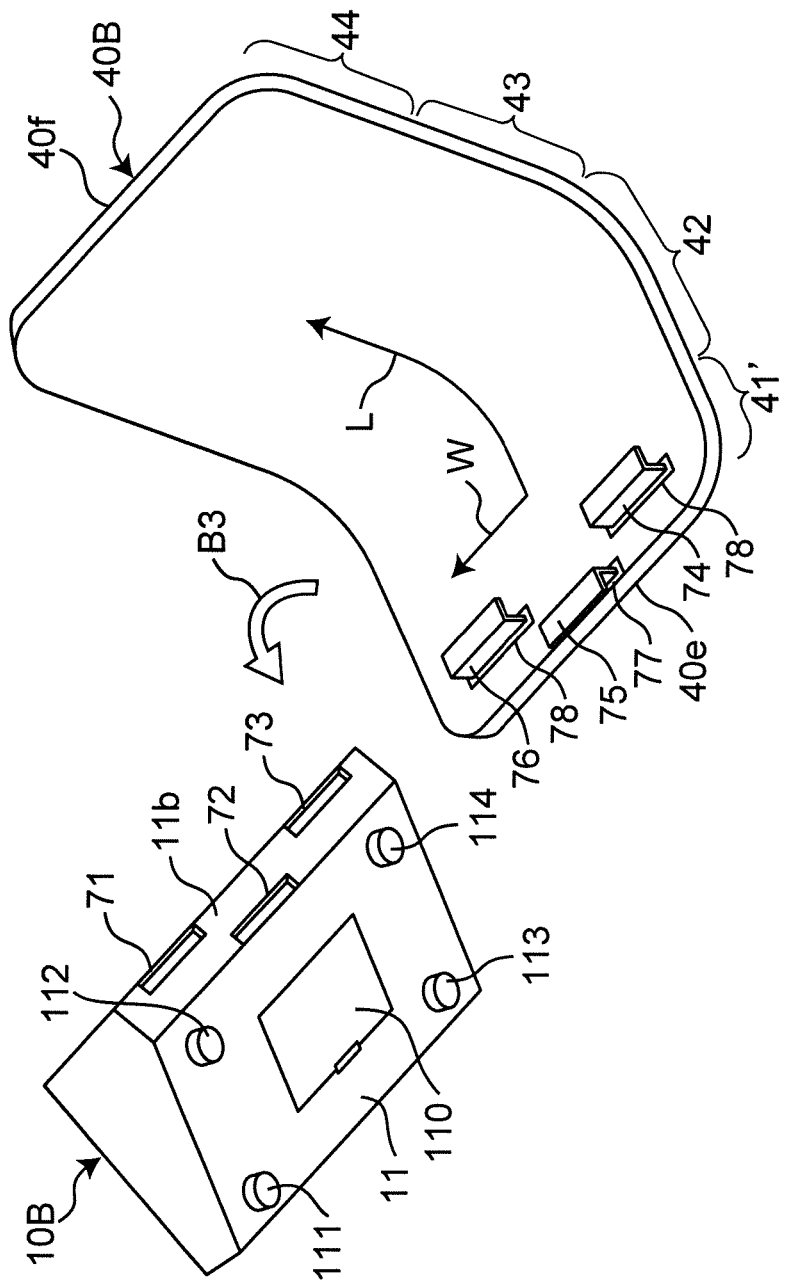
FIG. 12 is a diagram showing another modification of the structure in which the cover for a blood pressure meter is detachably attached to the main body.
Figure 13:
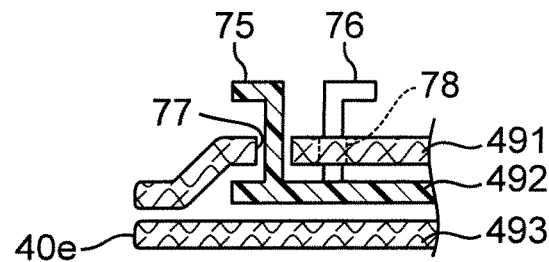
FIG. 13 is an enlarged cross-sectional view showing a configuration in the vicinity of a hook of the cover for a blood pressure meter of FIG. 12.
Figure 14:
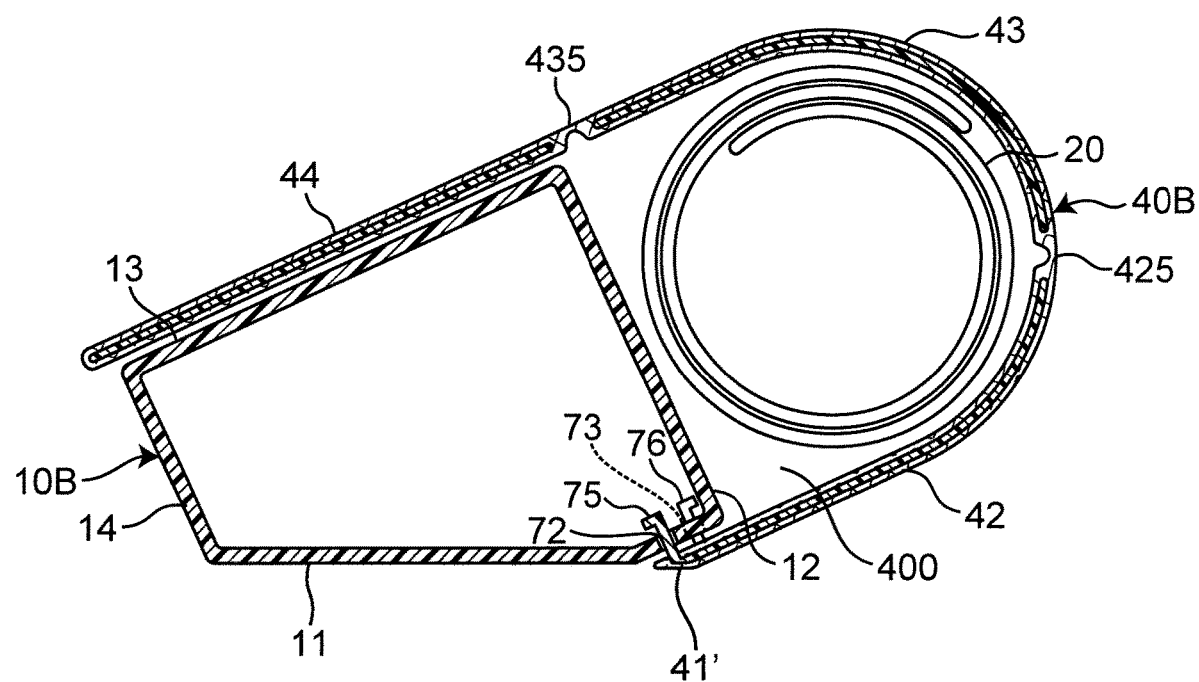
FIG. 14 is a cross-sectional view showing a state in which a cover for a blood pressure meter is attached to the main body of FIG. 12, and a panel cover region and a storage cover region are closed with respect to a front panel and a tray region.

FIGS. 12 to 14 show another modification of the structure in which the cover for a blood pressure meter 40 is detachably attached to the main body 10.

In this example, as shown in FIG. 12, a main body (indicated by reference numeral 10B) has a pair of right and left receiving holes 71 and 73 on the rear end side and a receiving hole 72 disposed at the center on the front end side in a rear edge portion 11b of a bottom surface 11. These receiving holes 71, 72, and 73 are configured as horizontally long openings (openings whose width dimension is longer than the depth dimension). On the other hand, a cover for a blood pressure meter (indicated by reference numeral 40B) has hooks 74, 75, and 76 with an L-shaped cross-section dimensioned so as to engage with the receiving holes 71, 72, and 73, respectively, in locations in a coupling region (indicated by reference numeral 41') corresponding to the receiving holes 71, 72, and 73. The front end of the central hook 75 is directed toward one end 40e side in a longitudinal direction L, and the front ends of the pair of right and left hooks 74 and 76 are directed toward the other end 40f side in the longitudinal direction L. These hooks 74, 75, and 76 are formed integrally with a core material 492 as illustrated for the hooks 75 and 76 in FIG. 13, and protrude to the outside through through holes 77 and 78 provided in an inner cloth 491.

When attaching the cover for a blood pressure meter 40B, as indicated by arrow B3 in FIG. 12, the user aligns and engages the hooks 74, 75, and 76 provided in the coupling region 41' of the cover for a blood pressure meter 40B with the receiving holes 71, 72, and 73 provided in the rear edge portion 11b of the bottom surface 11 of the main body 10B. FIG. 14 shows a state where the receiving holes 72 and 73 and the hooks 75 and 76 are engaged with each other (cover-coupled state). In this manner, the coupling region 41' is attached to the rear edge portion 11b of the bottom surface 11 of the main body 10B. Thus, the cover for a blood pressure meter 40B is easily attached to the main body 10B. Conversely, when removing the cover for a blood pressure meter 40B, the user removes the hooks 74, 75, and 76 from the receiving holes 71, 72, and 73, so that the coupling region 41' is removed from the rear edge portion 11b of the bottom surface 11 of the main body 10B. Thus, the cover for a blood pressure meter 40B is easily removed from the main body 10B.

In this example, as in the above example, the coupling region 41' only needs to face the rear edge portion 11b of the bottom surface 11. Accordingly, the dimension in the longitudinal direction L of the coupling region 41' (hence the cover for a blood pressure meter 40B) can be reduced as compared with a case where the coupling region 41 faces substantially the entire area of the bottom surface 11. That is, the cover for a blood pressure meter 40B can be downsized.

Figure 15:
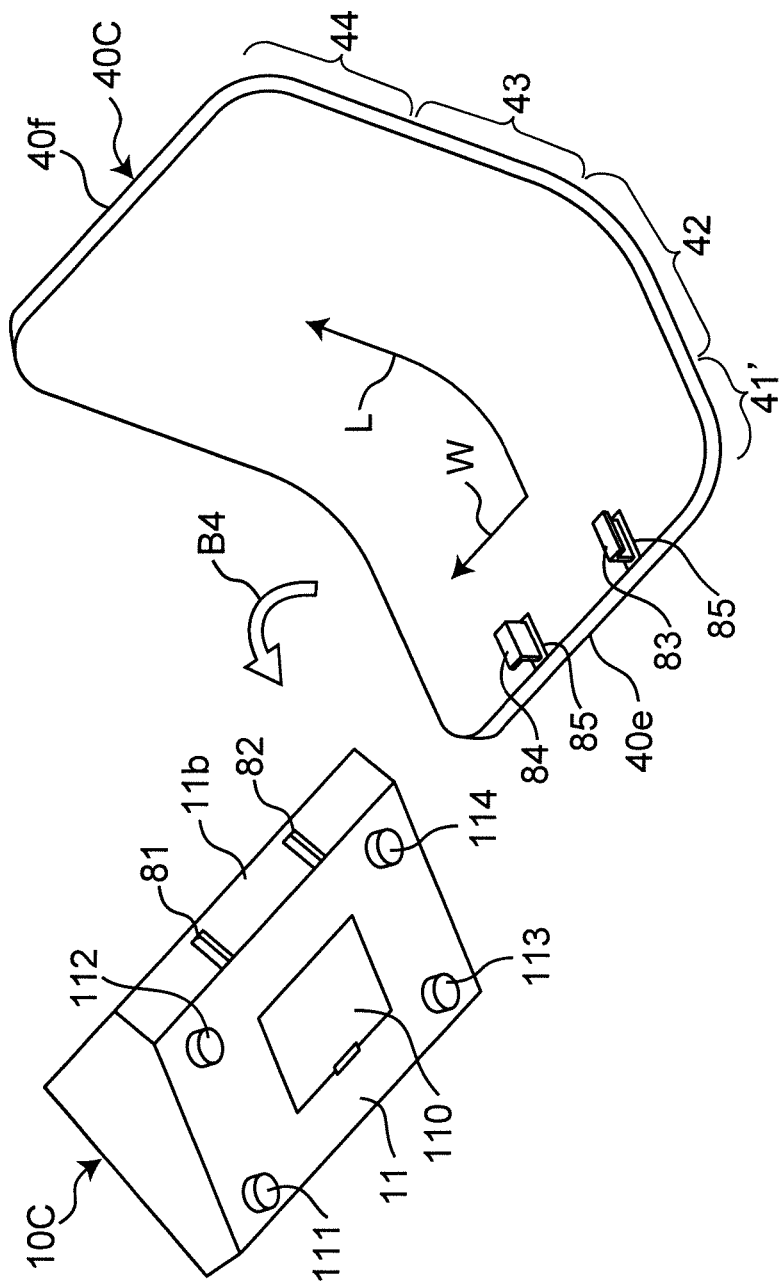
FIG. 15 is a diagram showing an example in which the number and arrangement of hooks of the cover for a blood pressure meter and the receiving holes of the main body of FIG. 14 are changed.

Note that the number and arrangement of the receiving holes 71, 72, and 73 and the hooks 74, 75, and 76 are not limited to those of the example shown in FIGS. 12 to 14. As shown in FIG. 15, receiving holes 81 and 82 on a main body (indicated by reference numeral 10C) side may be configured as a pair of vertically long openings (openings whose depth dimension is longer than the width dimension), and the tips of hooks 83 and 84 on a cover for a blood pressure meter (indicated by reference numeral 40C) side corresponding to the receiving holes 81 and 82 may be directed toward opposite sides in a width direction W. Similar to the hooks 74, 75, and 76 described above, these hooks 83 and 84 are each formed integrally with a core material 492, and protrude to the outside through the through holes 85 and 85 provided in an inner cloth 491. In the arrangement of FIG. 15, too, the cover for a blood pressure meter 40C is attached to the main body 10C (indicated by arrow B4 in FIG. 15) and removed in a reversed manner as similar to the example of FIGS. 12 to 14.

Modification 3

Figure 16:
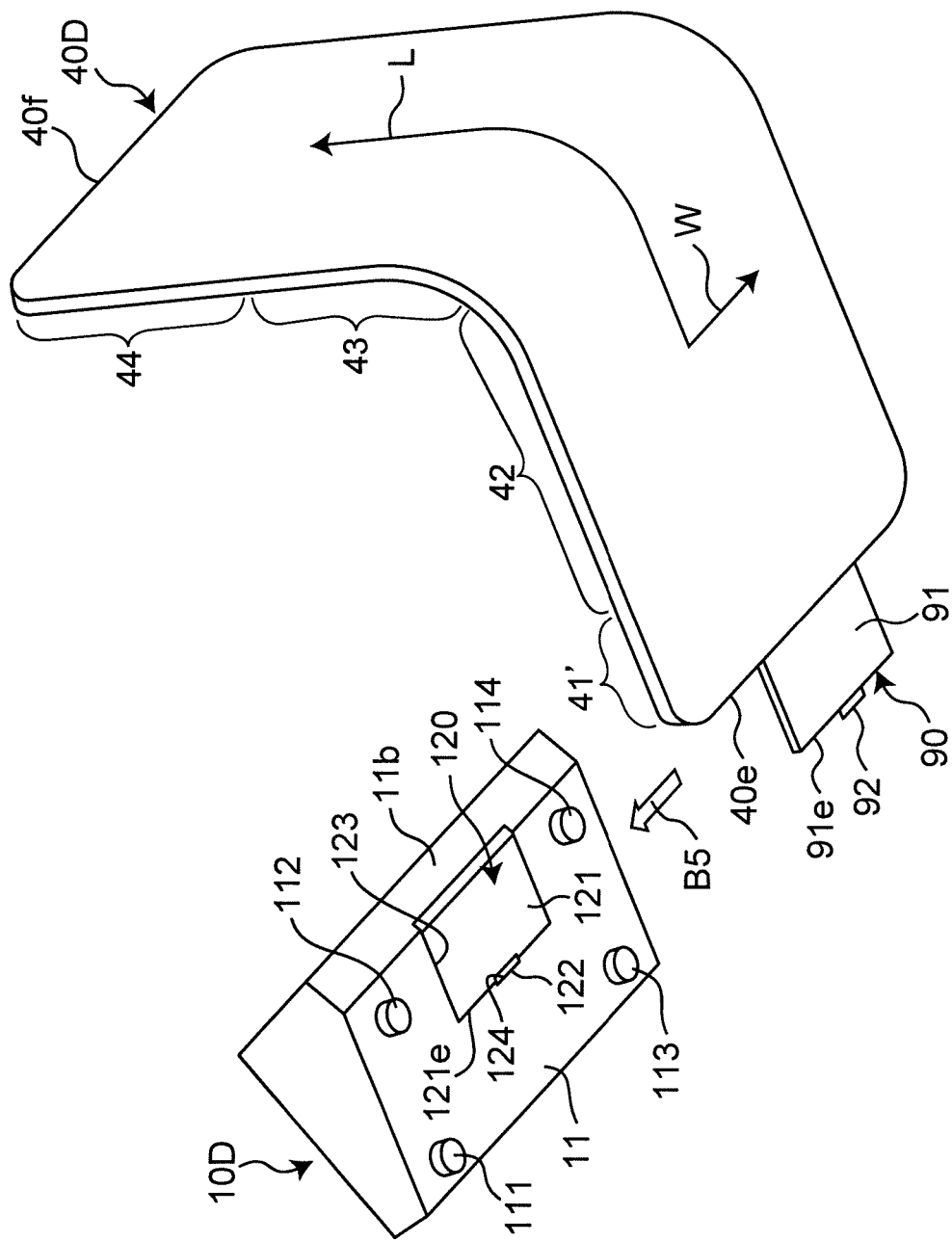
FIG. 16 is a diagram showing still another modification of the structure in which the cover for a blood pressure meter is detachably attached to the main body.
Figure 17:
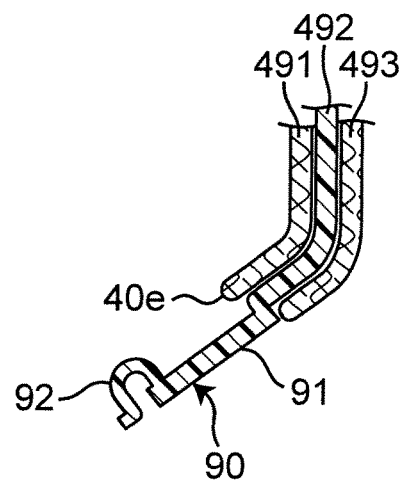
FIG. 17 is an enlarged cross-sectional view showing a configuration in the vicinity of a battery lid of the cover for a blood pressure meter of FIG. 16.
Figure 18:
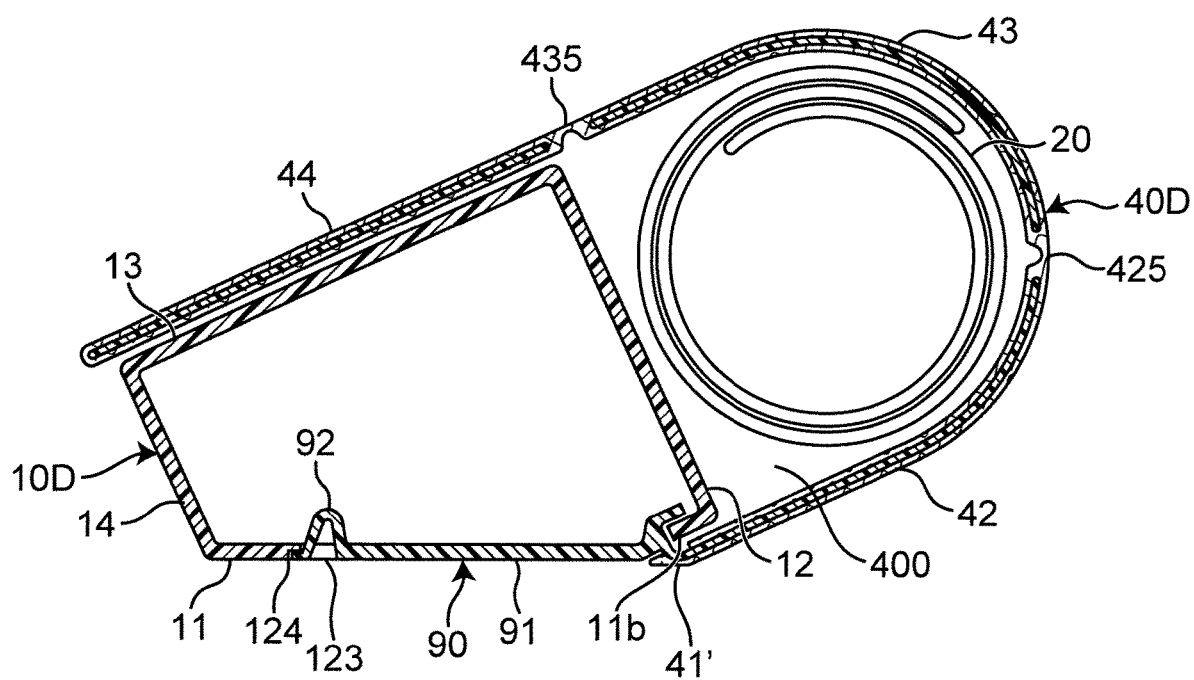
FIG. 18 is a cross-sectional view showing a state in which a cover for a blood pressure meter is attached to the main body in FIG. 16, and a panel cover region and a storage cover region are closed with respect to a front panel and a tray region.

FIGS. 16 to 18 show still another modification of the structure in which the cover for a blood pressure meter 40 is detachably attached to the main body 10.

In this example, as shown in FIG. 16, a main body (indicated by reference numeral 10D) has a substantially rectangular battery passage opening 123 formed in a bottom surface 11. In this example, the battery passage opening 123 is disposed in a position at the substantial center in the width direction (direction X shown in FIG. 1) and in contact with a rear edge portion 11b in the longitudinal direction (direction Y shown in FIG. 1) of a bottom surface 11. The battery passage opening 123 is an opening for inserting a battery into a battery storage portion (not shown) built in the main body 10 from the outside, or removing it. An original battery lid 120 as a first battery lid is detachably fitted and attached to the battery passage opening 123. Specifically, the battery lid 120 has a substantially rectangular plate portion 121 corresponding to the shape of the battery passage opening 123, and a hook portion 122 provided integrally at the substantial center of a front edge 121e of the plate portion 121. The battery lid 120 is detachably attached to the battery passage opening 123 by engaging the hook portion 122 with a cutout 124 provided in a corresponding part of the battery passage opening 123.

On the other hand, a cover for a blood pressure meter (indicated by reference numeral 40D) has a battery lid 90 for attaching the cover that is provided integrally with a coupling region (indicated by reference numeral 41'), and serves as a second battery lid having a shape that is detachably fitted to the battery passage opening 123. Specifically, the battery lid 90 has a substantially rectangular plate portion 91 corresponding to the shape of the battery passage opening 123, and a hook portion 92 provided integrally at the substantial center in a width direction W of an edge 91e of the plate portion 91. As shown in FIG. 17, the plate portion 91 of the battery lid 90 is formed integrally with a core material 492, and protrudes from one end 40e of an inner cloth 491 and an outer cloth 493.

When attaching the cover for a blood pressure meter 40D, the user first removes the original battery lid 120 from the battery passage opening 123 by releasing the engagement of the hook portion 122 with the cutout 124 shown in FIG. 16. Next, as indicated by arrow B5 in FIG. 16, the user fits the battery lid 90 of the cover for a blood pressure meter 40D into the battery passage opening 123 as shown in FIG. 18, in order to close the battery passage opening 123. At this time, the hook portion 92 engages with the cutout 124. In this manner, the battery lid 90 protruding from the coupling region 41' of the cover for a blood pressure meter 40D is attached to the bottom surface 11 of the main body 10D to form the cover-coupled state. Thus, the cover for a blood pressure meter 40D is easily attached to the main body 10D. Note that in the state where the battery lid 90 is attached to the main body 10D, the battery lid 90 prevents the battery accommodated in the battery storage portion from dropping off from the main body 10D. Conversely, when removing the cover for a blood pressure meter 40D, the user removes the battery lid 90 of the cover for a blood pressure meter 40D from the battery passage opening 123 by releasing the engagement of the hook portion 92 with the cutout 124. Thus, the cover for a blood pressure meter 40D is easily removed from the main body 10D.

In this example, as in the above example, the coupling region 41' only needs to face the rear edge portion 11b of the bottom surface 11. Accordingly, the dimension in a longitudinal direction L of the coupling region 41' can be reduced as compared with a case where the coupling region 41 faces substantially the entire area of the bottom surface 11. That is, a belt-like outer shape 490 of the cover for a blood pressure meter 40D can be downsized.

Note that the technique of attaching the cover using the battery lid is not limited to a blood pressure meter 1, and can be applied to general devices. That is, by applying this technique, a cover (represented by the same reference numeral as the cover for a blood pressure meter 40D) for covering an outer surface of a main body (represented by the same reference numeral as the main body 10 of the blood pressure meter 1) of a general device (represented by reference numeral 1000 (not shown)) can be detachably attached to the main body.

For example, this device 1000 is a device 1000 including a main body 10 and a cover 40D for covering an outer surface of the main body 10, in which:

the main body 10 has a first battery lid (represented by the same reference numeral as the aforementioned battery lid 120) having a shape that is detachably fitted to a battery passage opening (represented by the same reference numeral as the aforementioned battery passage opening 123) formed on the outer surface;

the cover 40D has an outer surface cover portion (represented by the same reference numerals as the aforementioned coupling region 41' to the aforementioned panel cover region 44) covering the outer surface of the device 1000, and a second battery lid (represented by the same reference numeral as the aforementioned battery lid 90) provided integrally with the outer surface cover portion 41' to 44 and having a shape that is detachably fitted to the battery passage opening 123; and when attaching the cover 40D, the second battery lid 90 is fitted in place of the first battery lid 120 to close the battery passage opening 123.

In the device 1000, in a state where the cover 40D is not attached to the main body 10 (cover non-coupled state), in order to close the battery passage opening 123 formed on the outer surface, the original first battery lid 120 is fitted to the battery passage opening 123. At this time, the device 1000 does not become bulky because of the cover 40D. Hence, the user can use the device 1000 in a small size. On the other hand, when attaching the cover 40D, the second battery lid 90 is fitted in place of the first battery lid 120 to close the battery passage opening 123. As a result, the cover 40D is attached to the main body 10 (cover-coupled state), and the outer surface of the main body 10 is covered and protected by the outer surface cover portion 41' to 44 of the cover 40D.

Modification 4

Figure 19:
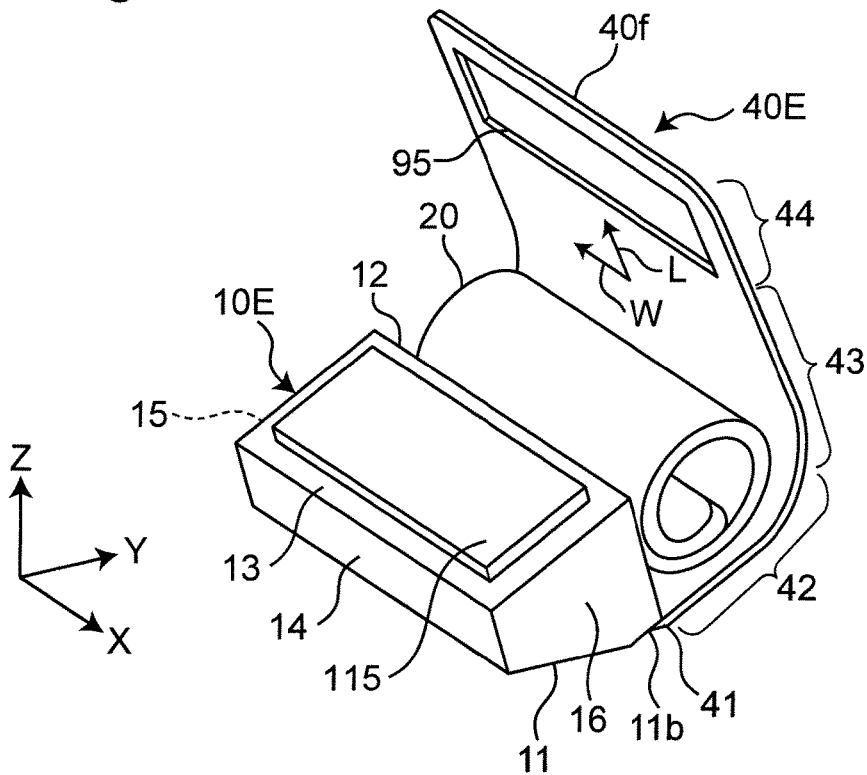
FIG. 19 is a diagram showing an additional structure for aligning the panel cover region of the cover for a blood pressure meter with the front panel of the main body.
Figure 20:
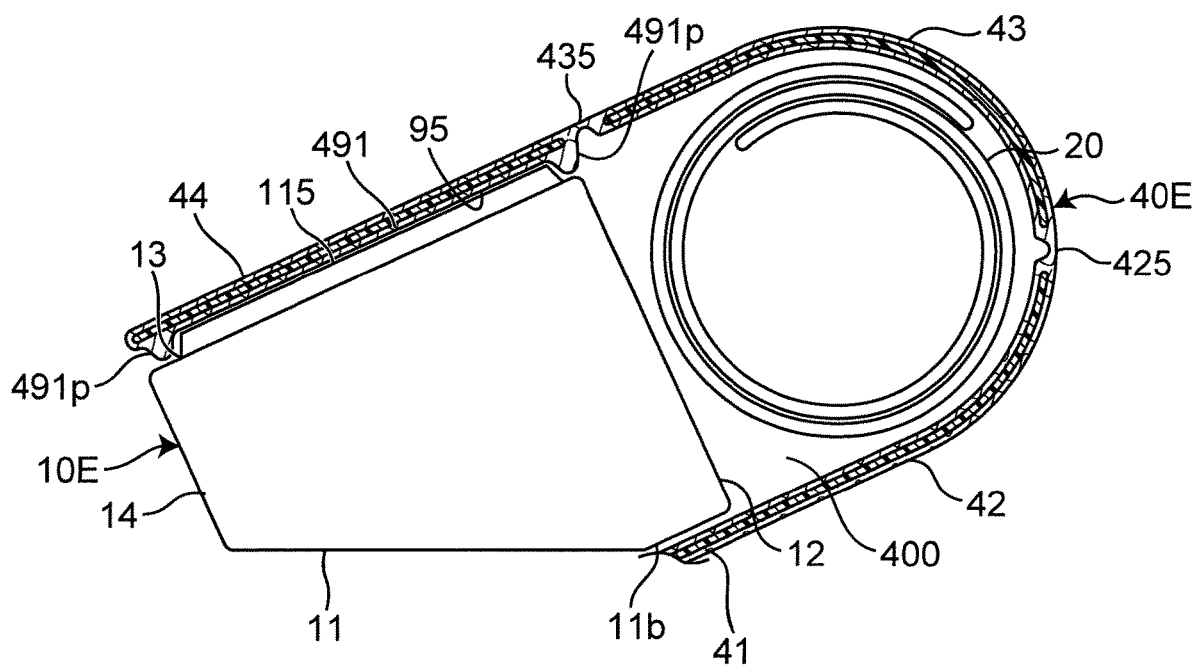
FIG. 20 is a cross-sectional view showing a state in which the panel cover region and a storage cover region are closed with respect to the front panel and a tray region of the blood pressure meter of FIG. 19.

FIGS. 19 to 20 show an additional structure for aligning the panel cover region 44 of the cover for a blood pressure meter 40 with respect to the front panel 13 of the main body 10.

In this example, as shown in FIG. 19, a main body (indicated by reference numeral 10E) has a raised portion 115 as a first undulation element slightly raised in a protruding manner (more precisely, a truncated pyramid shape) over substantially the entire area except for a peripheral edge portion of a front panel 13. Although not shown in FIG. 19 for the sake of simplicity, the above-described display 50 and operation portion 52 are provided on the raised portion 115. On the other hand, an inner cloth 491 side of a panel cover region 44 of a cover for a blood pressure meter (indicated by reference numeral 40E) has a depression 95 as a second undulation element having a shape to be fitted to the protruding raised portion 115 formed in the front panel 13 of the main body 10E, in a position corresponding to the raised portion 115. As shown in FIG. 20, the depression 95 is formed as a relatively recessed region by forming a portion 491p of the inner cloth 491 corresponding to the periphery of the raised portion 115 in a mountain shape.

Thus, when the panel cover region 44 and a storage cover region 43 are closed with respect to the front panel 13 and a tray region 42, for example, the panel cover region 44 is aligned with the front panel 13 of the main body 10E by fitting the depression 95 to the raised portion 115. Hence, it is possible to prevent a situation in which the panel cover region 44 is displaced relative to the front panel 13 of the main body 10E in a transverse direction A2 or a longitudinal direction A1 when viewed from the front as shown in FIG. 1, for example. Accordingly, the appearance is improved.

Note that while the first undulation element of the front panel 13 is the raised portion 115 and the second undulation element of the panel cover region 44 is the depression 95 in this example, the invention is not limited to this. The first undulation element and the second undulation element only need to be used for alignment, and conversely to this example, the first undulation element may be in a recessed shape and the second undulation element may be in a protruding shape. Additionally, the region of the front panel 13 occupied by the first undulation element (hence the region of the panel cover region 44 occupied by the second undulation element) may be small instead of substantially the entire area.

Modification 5

Figure 21:
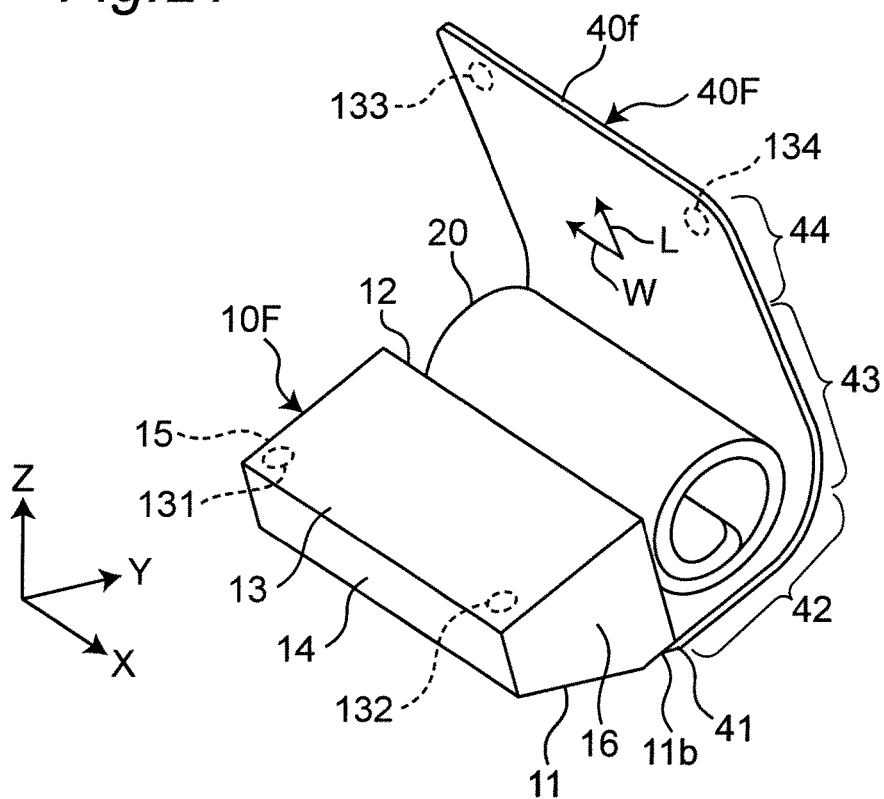
FIG. 21 is a diagram showing another additional structure for aligning the panel cover region of the cover for a blood pressure meter with the front panel of the main body.
Figure 22:
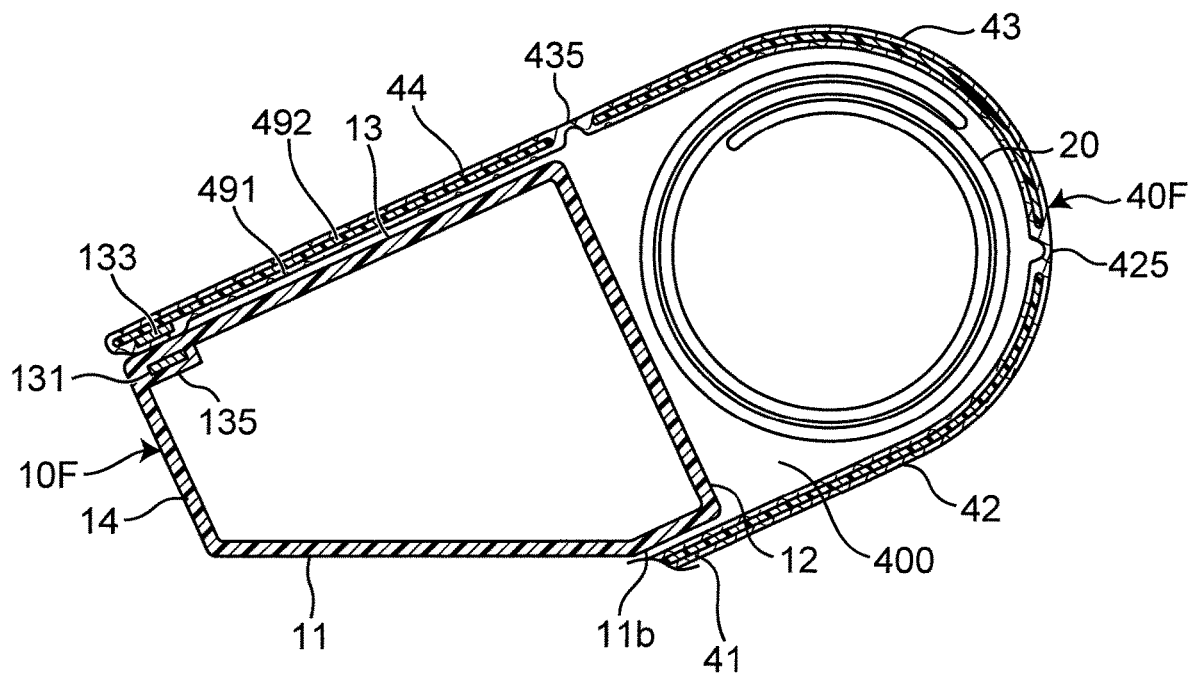
FIG. 22 is a cross-sectional view showing a state in which the panel cover region and the storage cover region are closed with respect to the front panel and the tray region of the blood pressure meter of FIG. 20.

FIGS. 21 to 22 show another additional structure for aligning the panel cover region 44 of the cover for a blood pressure meter 40 with respect to the front panel 13 of the main body 10.

In this example, as shown in FIG. 21, a main body (indicated by reference numeral 10F) incorporates magnets 131 and 132 as first magnetic elements in the right and left corner areas on the front edge side of the front panel 13, respectively. On the other hand, a panel cover region 44 of a cover for a blood pressure meter (indicated by reference numeral 40F) incorporates magnets 133 and 134 as second magnetic elements that attract and are attracted by the first magnetic elements by magnetic force, in positions corresponding to the magnets 131 and 132 incorporated in the front panel 13 of the main body 10F, respectively. Specifically, as illustrated for the magnet 131 in FIG. 22, the magnets 131 and 132 are held in a magnet holding portion 135 provided along the front panel 13 of the main body 10F. Additionally, as illustrated for the magnet 133 in FIG. 22, the magnets 133 and 134 are held between an inner cloth 491 and a core material 492 in the panel cover region 44 (bonded to the core material 492 by an adhesive (not shown) in this example.).

Thus, when the panel cover region 44 and a storage cover region 43 are closed with respect to the front panel 13 and a tray region 42, for example, the panel cover region 44 is aligned with the front panel 13 of the main body 10F by the attraction between the magnets 131 and 132 and the magnets 133 and 134 by magnetic force. Hence, it is possible to prevent a situation in which the panel cover region 44 is displaced relative to the front panel 13 of the main body 10F in a transverse direction A2 or a longitudinal direction A1 when viewed from the front as shown in FIG. 1, for example. Accordingly, the appearance is improved.

Note that the combination of the "first magnetic element" and the "second magnetic element" that are attracted to each other by magnetic force is not limited to the combination of the magnets 131 and 132 and the magnets 133 and 134 as in this example, and a combination of a magnet and a magnetic material can be adopted.

Modification 6

Figure 23:
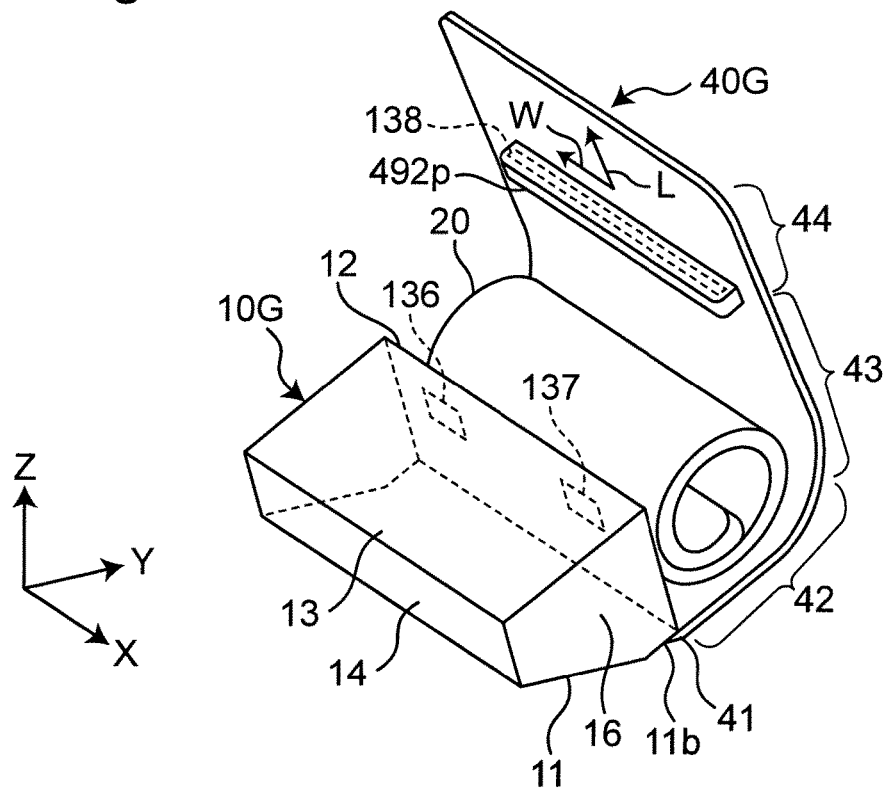
FIG. 23 is a diagram showing still another additional structure for aligning the panel cover region of the cover for a blood pressure meter with the front panel of the main body.
Figure 24:
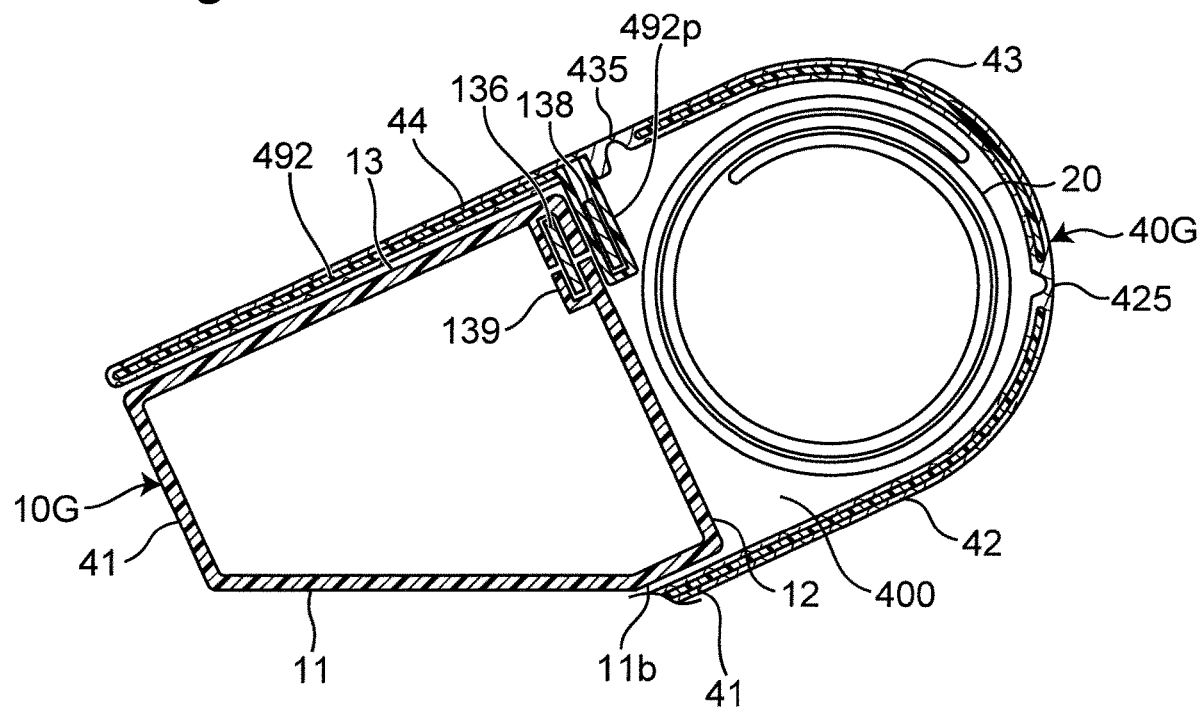
FIG. 24 is a cross-sectional view showing a state in which the panel cover region and the storage cover region are closed with respect to the front panel and the tray region of the blood pressure meter of FIG. 23.

FIGS. 23 to 24 show still another additional structure for aligning the panel cover region 44 of the cover for a blood pressure meter 40 with the front panel 13 of the main body 10.

In this example, as shown in FIG. 23, a main body (indicated by reference numeral 10G) incorporates magnets 136 and 137 as first magnetic elements on the right and left sides of a back surface 12, respectively. On the other hand, in a panel cover region 44 of a cover for a blood pressure meter (indicated by reference numeral 40G), a bar-shaped iron piece 138 as a second magnetic element that attracts and is attracted by the first magnetic elements is provided so as to correspond to both the magnets 136 and 137 incorporated in a front panel 13 of the main body 10G. Specifically, as illustrated for the magnet 136 in FIG. 24, the magnets 136 and 137 are held in a magnet holding portion 139 provided along the back surface 12 of the main body 10G. Additionally, as illustrated in FIG. 24, the iron piece 138 is surrounded and held in an iron piece holding portion 492p formed integrally with a core material 492 of the panel cover region 44. In this example, the iron piece holding portion 492p is formed by forming an end portion of the core material 492 of the panel cover region 44 on a second boundary portion 435 side into a U shape in cross section, and making it protrude from an inner cloth 491.

Thus, when the panel cover region 44 and a storage cover region 43 are closed with respect to the front panel 13 and a tray region 42, for example, the panel cover region 44 is aligned with the front panel 13 of the main body 10G by the attraction between the magnets 136 and 137 and the iron piece 138 by magnetic force. Hence, it is possible to prevent a situation in which the panel cover region 44 is displaced relative to the front panel 13 of the main body 10G in a transverse direction A2 or a longitudinal direction A1 when viewed from the front as shown in FIG. 1, for example. Accordingly, the appearance is improved.

Modification 7

Figure 25:
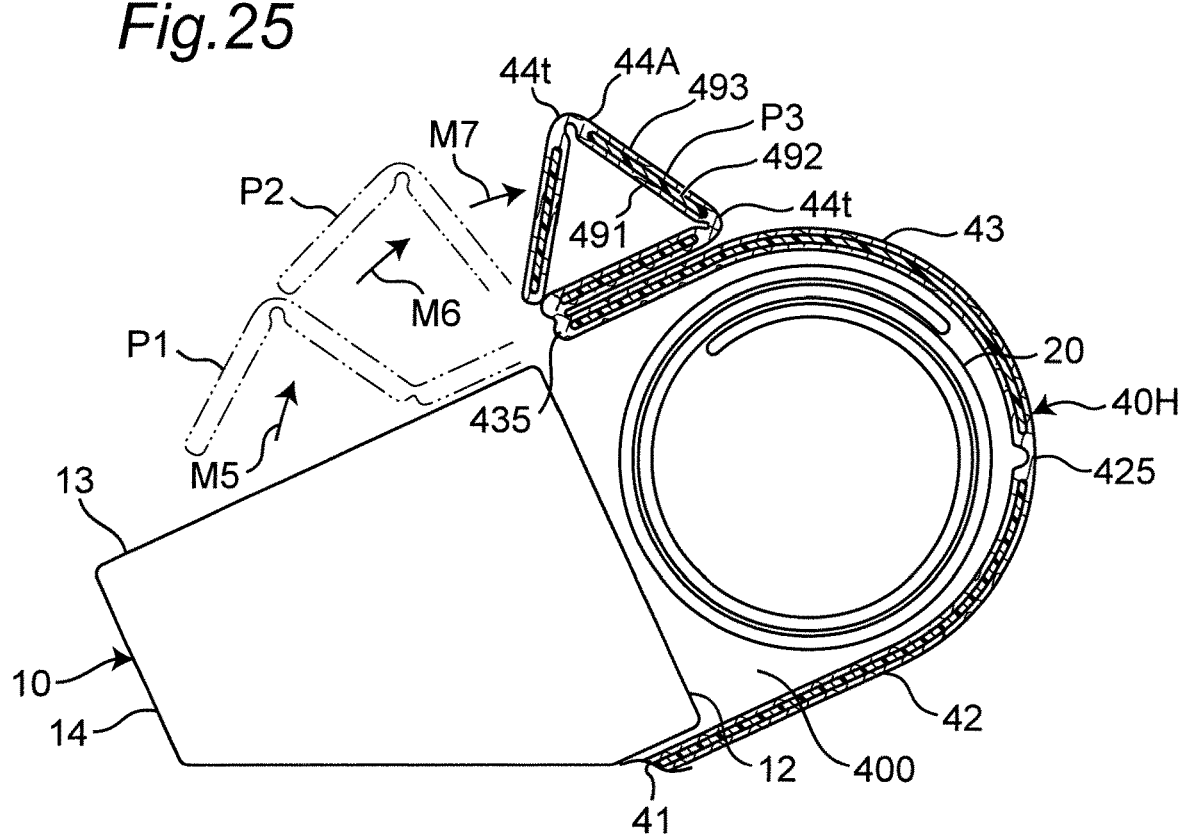
FIG. 25 is a cross-sectional view showing a modification of the panel cover region of the cover for a blood pressure meter.

FIG. 25 shows a modification of the panel cover region 44 of the cover for a blood pressure meter 40.

In this example, in a panel cover region (indicated by reference numeral 44A) of a cover for a blood pressure meter (indicated by reference numeral 40H), a core material 492 is divided into three equal parts in a longitudinal direction L by two gaps 44*t* and 44*t*. The panel cover region 44A is formed only of an inner cloth 491 and an outer cloth 493 at the gaps 44*t* and 44*t*, and is configured to be soft enough to bend by the weight of each of the three divided parts. Note that at the gaps 44*t* and 44*t*, the inner cloth 491 and the outer cloth 493 are in contact with each other and sewn. Accordingly, the core material 492 does not move across each of the gaps 44*t* and 44*t* in the longitudinal direction L in the panel cover region 44A.

As a result, as shown in FIG. 25, when the panel cover region 44A is opened with respect to the front panel 13 as indicated by arrows M5, M6, and M7 in the cover-coupled state while a storage cover region 43 covers a tray region 42, the panel cover region 44A is folded at two locations (gaps 44*t* and 44*t*) in the longitudinal direction L. In this example, the panel cover region 44A takes relatively small postures P1, P2, and P3 in the process of being opened, as compared with the flat panel cover region 44. Accordingly, the user can open the panel cover region 44A easily with a smaller hand movement. The opened panel cover region 44A maintains the relatively small posture P3 by its own weight.

Modification 8

Figure 26:
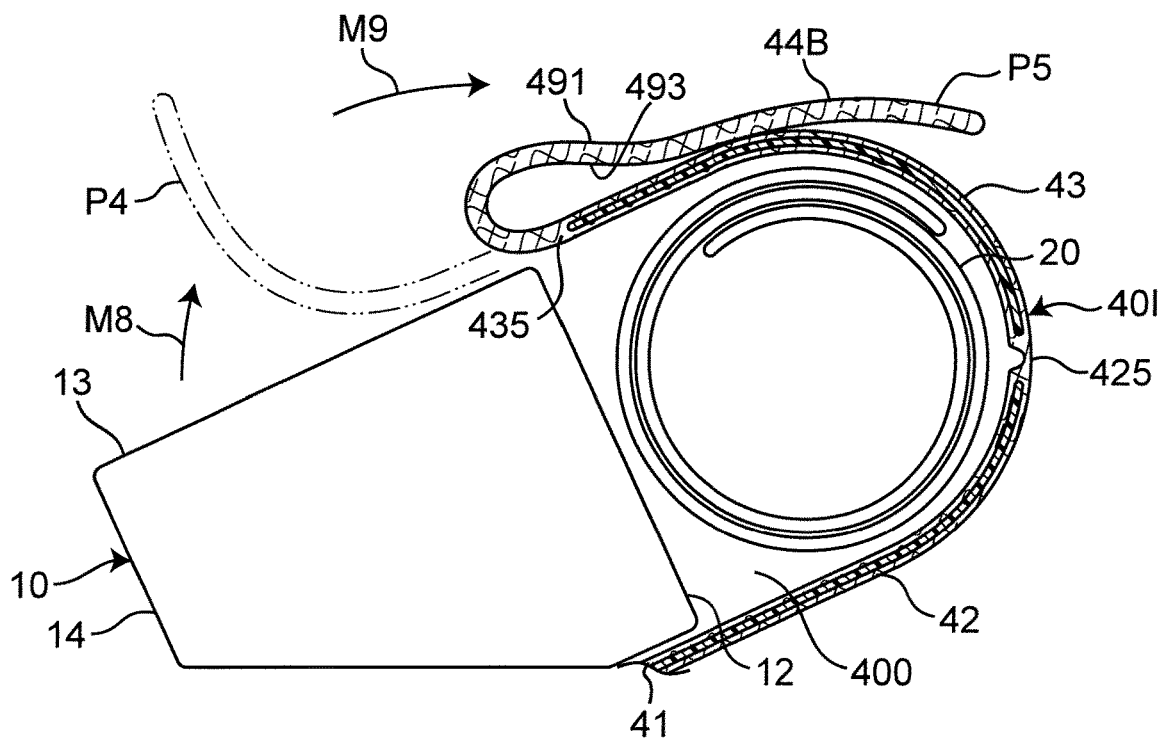
FIG. 26 is a cross-sectional view showing another modification of the panel cover region of the cover for a blood pressure meter.

FIG. 26 shows another modification of the panel cover region 44 of the cover for a blood pressure meter 40.

In this example, a panel cover region (indicated by reference numeral 44B) of a cover for a blood pressure meter (indicated by reference numeral 40I) is formed only of an inner cloth 491 and an outer cloth 493, and a core material 492 is omitted. Hence, the panel cover region 44B is flexible in a longitudinal direction L, and is configured to be soft enough to bend by the weight of the panel cover region 44B.

As a result, as shown in FIG. 26, when the panel cover region 44B is opened with respect to a front panel 13 as indicated by arrows M8 and M9 in the cover-coupled state while a storage cover region 43 covers a tray region 42, the panel cover region 44B is flexed in the longitudinal direction L. In this example, the panel cover region 44B takes relatively small postures P4 and P5 in the process of being opened, as compared to the flat panel cover region 44. Accordingly, the user can open the panel cover region 44B easily with a smaller hand movement. The opened panel cover region 44B maintains the relatively small posture P5 by its own weight.

Modification 9

Figure 27:
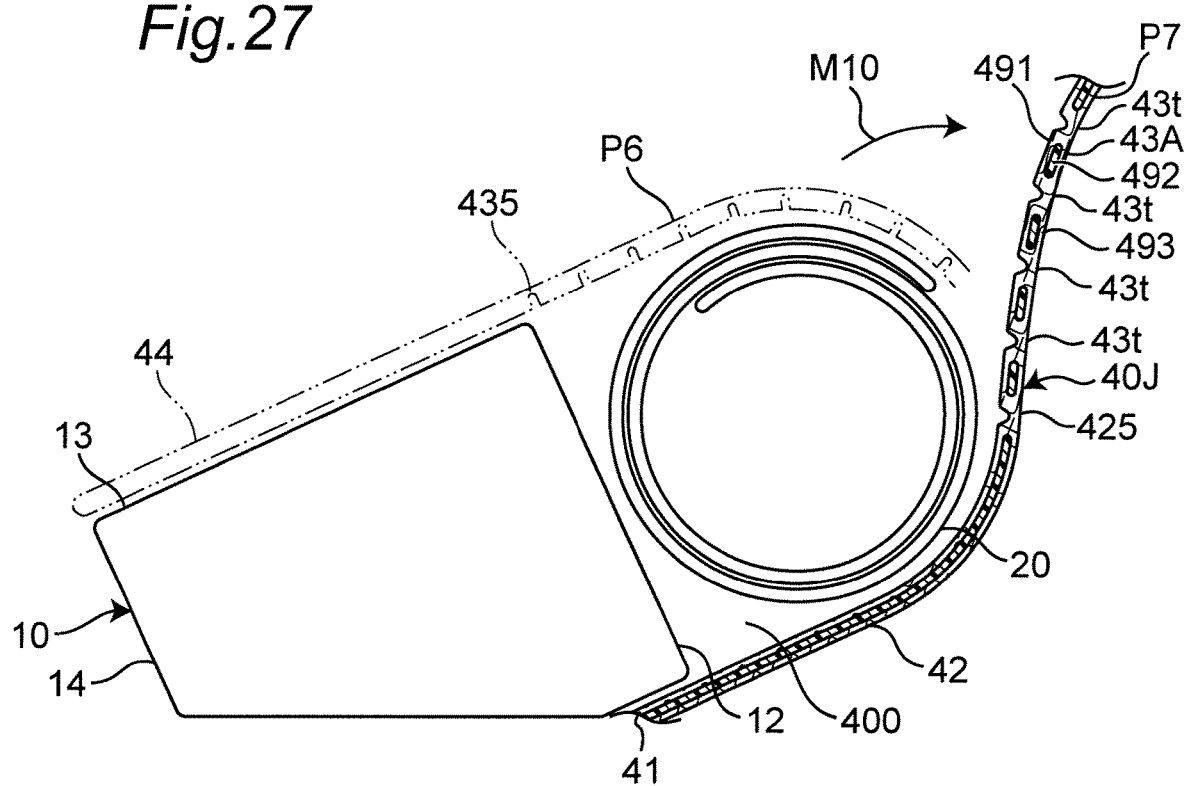
FIG. 27 is a cross-sectional view showing a modification of the storage cover region of the cover for a blood pressure meter.

FIG. 27 shows a modification of the storage cover region 43 of the cover for a blood pressure meter 40.

In this example, in a storage cover region (indicated by reference numeral 43A) of a cover for a blood pressure meter (indicated by reference numeral 40J), a core material 492 is divided in to multiple (many) equal parts in a longitudinal direction L by many (four or more) gaps 43*t*, 43*t*, . . . . The storage cover region 43A is formed only of an inner cloth 491 and an outer cloth 493 at the gaps 43*t*, 43*t*, . . . , and is configured to be soft enough to bend by the weight of each of the multiple divided parts.

Note that at the gaps 43*t*, 43*t*, . . . , the inner cloth 491 and the outer cloth 493 are in contact with each other and sewn. Accordingly, the core material 492 does not move across each of the gaps 43*t*, 43*t*, . . . in the storage cover region 43A in the longitudinal direction L.

As a result, as shown in FIG. 27, when the storage cover region 43A is opened with respect to a tray region 42 as indicated by arrow M10 in the cover-coupled state, the storage cover region 43A is folded (takes postures P6 and P7 when being opened in this example) at many locations (gaps 43*t*, 43*t*, . . . ) in the longitudinal direction L. Accordingly, the user can open the storage cover region 43A easily.

Modification 10

Figure 28:
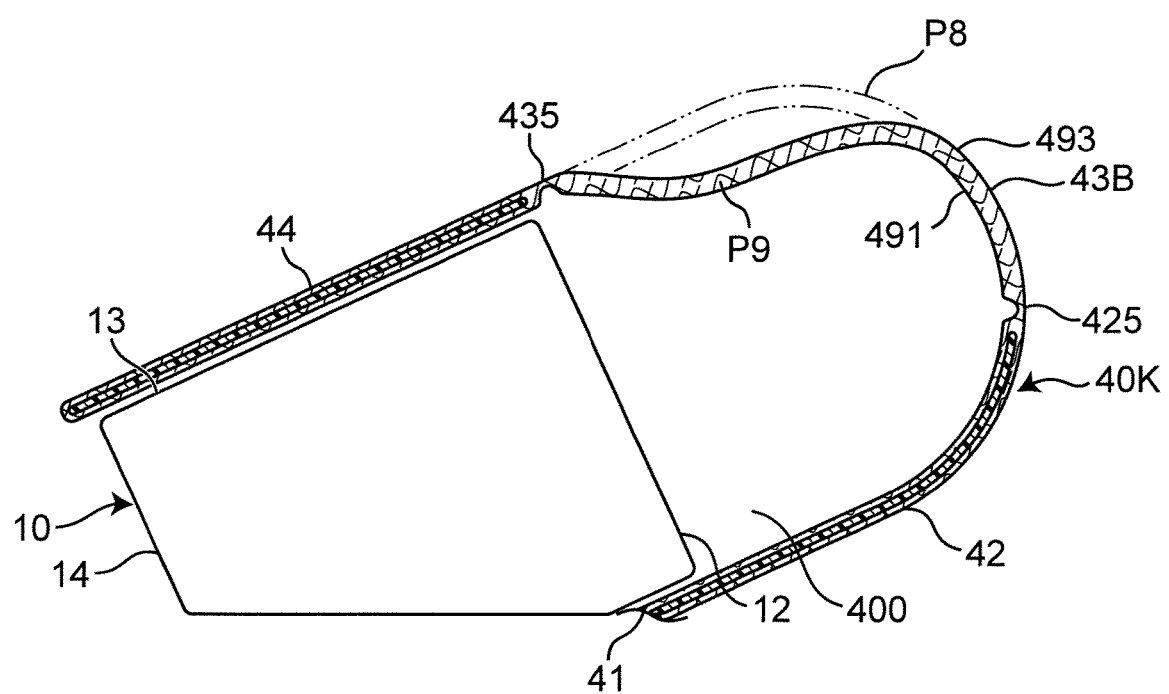
FIG. 28 is a cross-sectional view showing another modification of the storage cover region of the cover for a blood pressure meter.

FIG. 28 shows another modification of the storage cover region 43 of the cover for a blood pressure meter 40.

In this example, a storage cover region (indicated by reference numeral 43B) of a cover for a blood pressure meter (indicated by reference numeral 40K) is formed only of an inner cloth 491 and an outer cloth 493, and a core material 492 is omitted. Hence, the storage cover region 43B is flexible in a longitudinal direction L, and is configured to be soft enough to bend by the weight of the storage cover region 43B.

In this example, as in the previous example, the user can open the storage cover region 43B easily. Note that in this example, as shown in FIG. 28, the storage cover region 43B takes a posture P9 where it sags by its own weight in the cover-coupled state and in the state where a panel cover region 44 and the storage cover region 43 are closed with respect to a front panel 13 and a tray region 42. Note that the above-described storage cover region 43 having the core material 492 can take an upwardly projecting posture P8.

Modification 11

Figure 29:
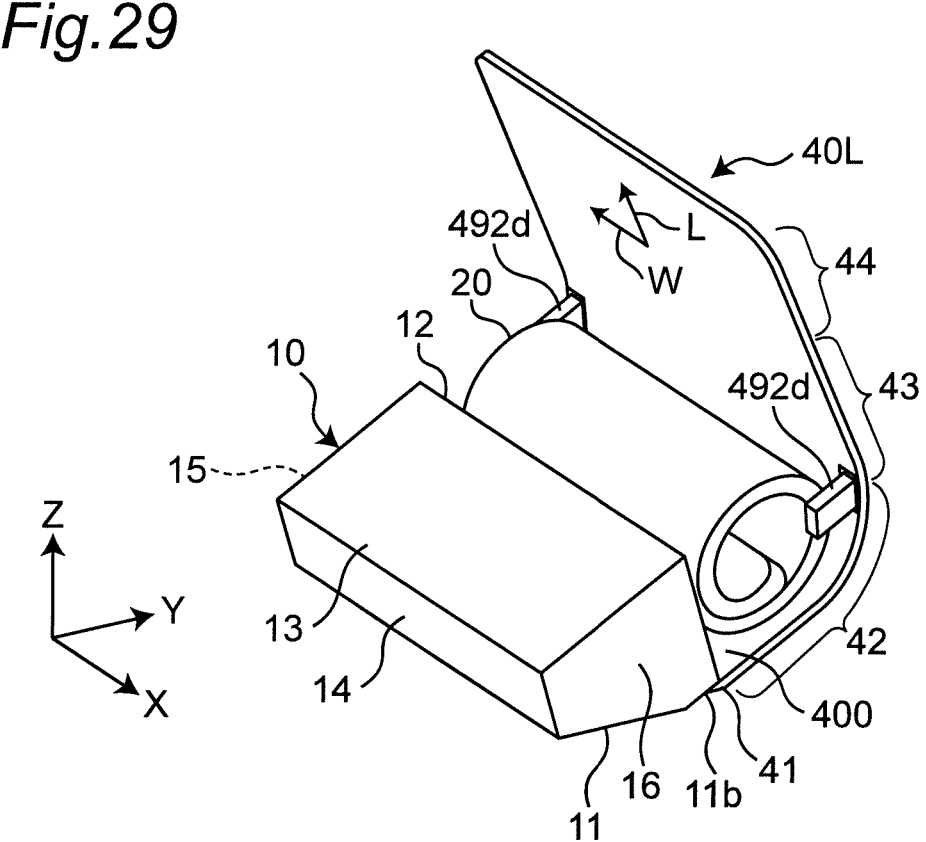
FIG. 29 is a diagram showing an additional structure for preventing the cuff belt received in the tray region from jumping out to the side.
Figure 30:
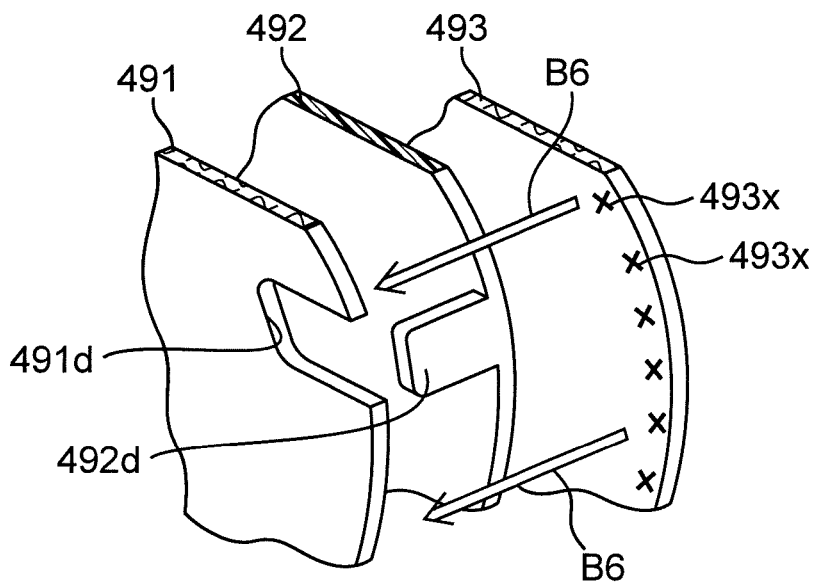
FIG. 30 is an enlarged diagram showing a configuration of the vicinity of a stopper element of the cover for a blood pressure meter of FIG. 29.

FIGS. 29 and 30 show an additional structure for preventing the cuff belt 20 received in the tray region 42 from jumping out to the side.

In this example, as shown in FIG. 29, a pair of substantially rectangular plate-like stopper elements 492*d* and 492*d* protruding forward (−Y direction) are provided in both edge portions in a width direction W of a tray region 42 of a cover for a blood pressure meter (indicated by reference numeral 40L). As illustrated for the near-side stopper element 492*d* in FIG. 30, these stopper elements 492*d* and 492*d* are formed integrally with a core material 492, and protrude forward through a cutout 491*d* provided in an inner cloth 491. Note that the inner cloth 491 and an outer cloth 493 are brought into contact with each other as indicated by arrows B6, and are sewn along seams 493*x*, 493*x*, . . . .

In this example, as shown in FIG. 29, for example, in a state where a cuff belt 20 is placed in a space 400 where a back surface 12 of a main body 10 and the tray region 42 face each other, it is possible to prevent the cuff belt 20 from needlessly jumping out to the side.

Figure 31:
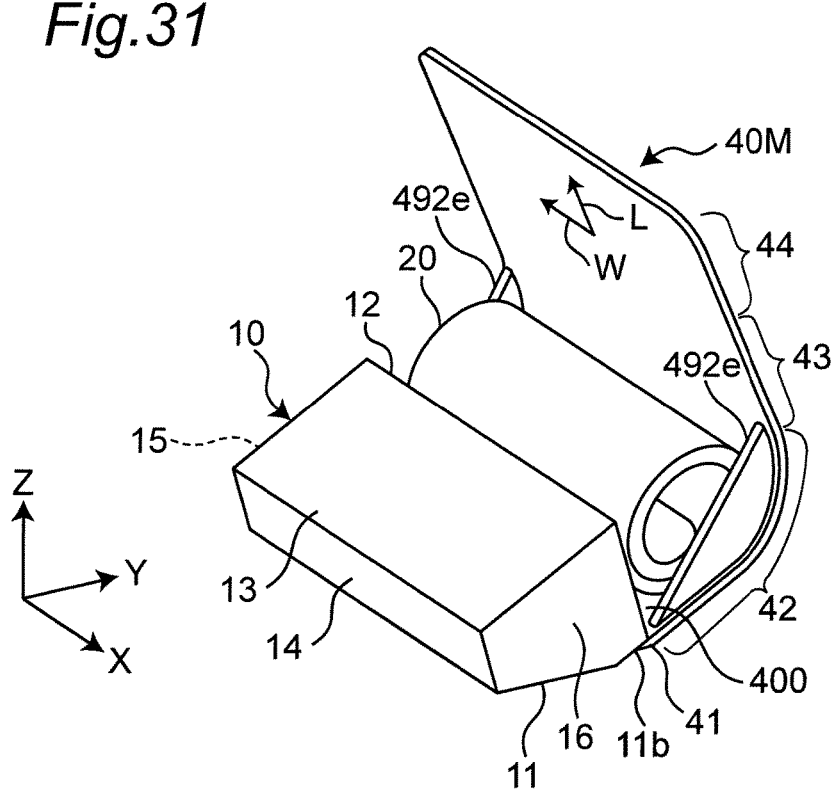
FIG. 31 is a diagram showing another additional structure for preventing the cuff belt received in the tray region from jumping out to the side.

The shape of the stopper element is not limited to a substantially rectangular plate shape as in the above example. As in a cover for a blood pressure meter (indicated by reference numeral 40M) shown in FIG. 31, substantially semicircular plate-like stopper elements 492*e* and 492*e* may be provided in both edge portions in a width direction W of a tray region 42. In this case, too, as in the example of FIGS. 29 and 30, in a state where a cuff belt 20 is placed in a space 400 where a back surface 12 of a main body 10 and a tray region 42 face each other, it is possible to prevent the cuff belt 20 from needlessly jumping out to the side.

Note that if the stopper element covers the entire side region of the space 400, it is difficult for the user to place the cuff belt 20 in the space 400 or to remove the cuff belt 20 from the space 400. Hence, it is desirable that the stopper element does not cover the entire side region of the space 400 but only a part thereof (Design of Cover for Blood Pressure Meter)

In a typical example, as shown in FIG. 2A, in the cover-coupled state and particularly in a state where the cuff belt 20 having an outer diameter of 80 mm is accommodated in a cuff storage portion, the heights of the front edge portion 13a and the rear edge portion 13b of the front panel 13 of the main body 10 are set to 40 mm and 84 mm, respectively. The depth from the front edge portion 13a of the front panel 13 to the rear edge portion 11b of the bottom surface 11 of the main body 10 is set to 126 mm. The height from a lower surface of the coupling region 41 to the top of the storage cover region 43 of the cover for a blood pressure meter 40 is set to 116 mm. The depth from the front end (other end 40f) of the cover for a blood pressure meter 40 to the rear end (generally, a first boundary portion 425) of the cover for a blood pressure meter 40 is set to 202 mm. As shown in FIG. 2B, the width of the main body 10 (width between a left side surface 15 and a right side surface 16) is set to 170 mm. The width of the cover for a blood pressure meter 40 is set to 176 mm.

Figure 32A:
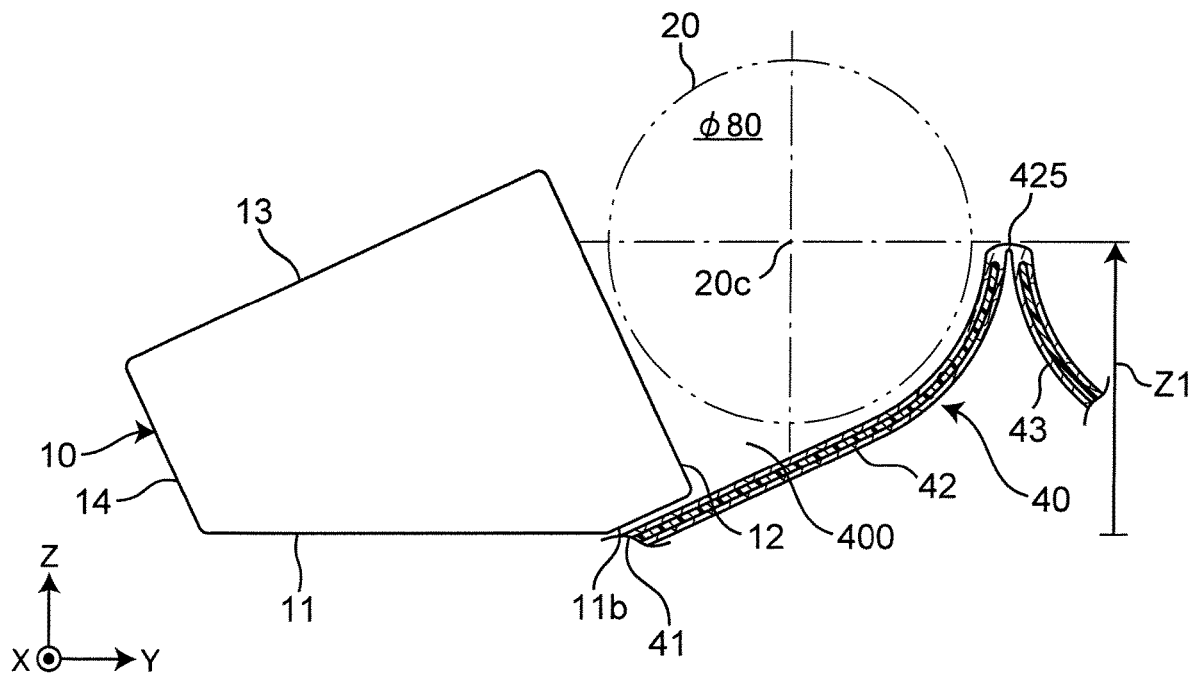
FIG. 32A is a diagram illustrating the setting of a height of an upper end of the tray region of the blood pressure meter.

Additionally, as shown in FIG. 32A, a height Z1 of the upper end (i.e., the first boundary portion 425) of the tray region 42 in the cover-coupled state is set to be the same height as a center line 20c of the cuff belt 20 (the outer diameter is 80 mm in this example) rolled into a roll shape and received in the tray region 42 in this example.

Figure 32B:
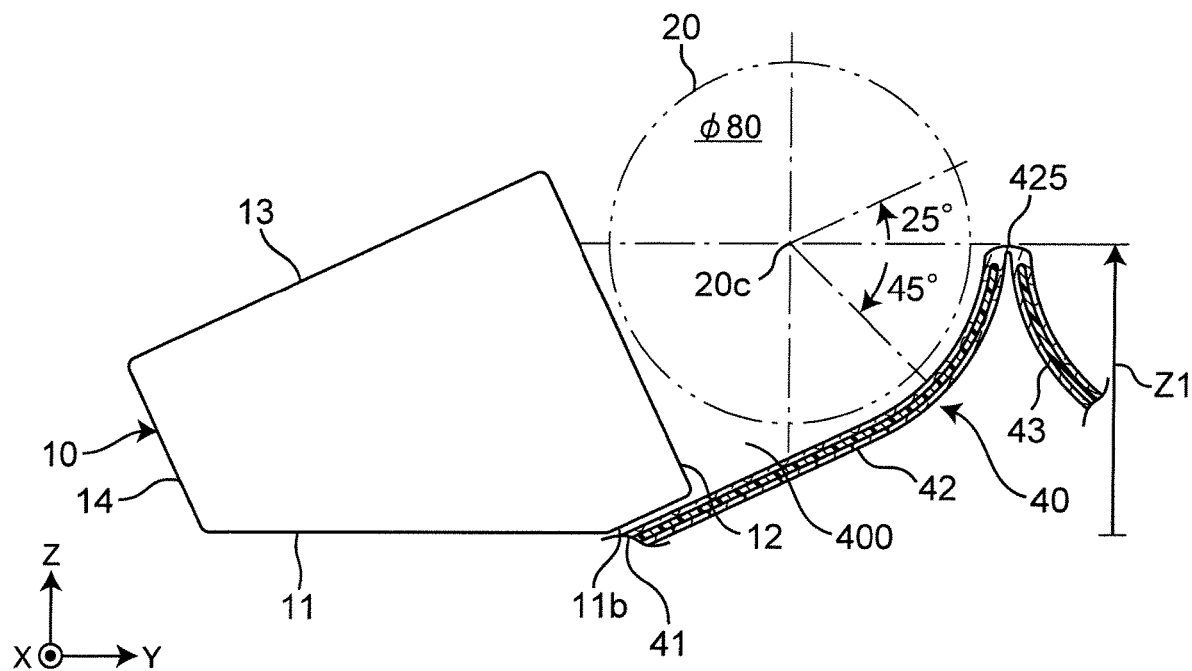
FIG. 32B is a diagram illustrating an allowable setting range of the height of the upper end of the tray region of the blood pressure meter.

However, the present invention is not limited to this. As shown in FIG. 32B, the height Z1 of the upper end 425 of the tray region 42 in the cover-coupled state only needs to be set within a range between an angle of depression of 45 degrees and an angle of elevation of 25 degrees when viewed from the center line 20c of the cuff belt 20 rolled into a roll shape and received in the tray region 42. If the height Z1 of the upper end 425 of the tray region 42 is set to be higher than the angle of depression of 45 degrees when viewed from the center line 20c of the cuff belt 20, even when the panel cover region 44 and the storage cover region 43 are opened with respect to the front panel 13 and the tray region 42 and laid down, the upper end 425 of the tray region 42 prevents the cuff belt 20 from falling backward (+Y direction) from the tray region 42. If the height Z1 of the upper end 425 of the tray region 42 is set to be lower than the angle of elevation of 25 degrees when viewed from the center line 20c of the cuff belt 20, when the panel cover region 44 and the storage cover region 43 are opened with respect to the front panel 13 and the tray region 42, the cuff belt 20 rolled into a roll shape can be easily placed in or removed from the space 400 where the back surface 12 of the main body 10 and the tray region 42 face each other.

While the outer diameter of the cuff belt 20 rolled into a roll shape is 80 mm in the above example, the invention is not limited to this. For example, it is assumed that the value of the outer diameter of the cuff belt 20 rolled into a roll falls within the range of 60 mm to 95 mm. Compared with the cuff belt 20 having an outer diameter of 80 mm, a cuff belt having an outer diameter of 95 mm is more likely to fall back (+Y direction) from the tray region 42. Hence, from the viewpoint of preventing the fall, it is desirable to set the lower limit (angle of depression of 45 degrees) of the height Z1 of the upper end 425 of the tray region 42 assuming that the cuff belt has an outer diameter of 95 mm. On the other hand, compared with the cuff belt 20 having an outer diameter of 80 mm, a cuff belt having an outer diameter of 60 mm is difficult to put in and out of the tray region 42. Hence, from the viewpoint of easy insertion and removal, it is desirable to set the upper limit (angle of elevation of 25 degrees) of the height Z1 of the upper end 425 of the tray region 42 assuming that the cuff belt has an outer diameter of 60 mm.

Note that in the above-described embodiment, the cuff belt 20 is rolled into a roll shape. However, the present invention is not limited to this. When the user rolls the cuff belt 20 into a roll shape after blood pressure measurement is completed, a folded air tube 38 may be wound around the center of the cuff belt 20 and placed in the tray region 42. Additionally, when the cuff belt 20 is rolled into a roll shape, the air tube 38 folded between the spiral layers formed by the cuff belt 20 may be wound together and placed in the tray region 42. In this case, the rolled cuff belt 20 may have a cylindrical shape with a slightly distorted cross section.

Additionally, the folded air tube 38 may first be placed in the tray region 42, and the cuff belt 20 rolled into a roll shape may be placed thereon. Conversely, the cuff belt 20 rolled into a roll shape may first be placed in the tray region 42, and the folded air tube 38 may be placed thereon. Additionally, the user may fold the cuff belt 20 into a flat layer shape instead of rolling the cuff belt 20 into a roll, and place the cuff belt 20 in the tray region 42 on top of or below the folded air tube 38.

In the above-described embodiment, the front panel 13 of the main body 10 of the blood pressure meter 1 is an inclined surface extending at an angle of about 25 degrees with respect to the horizontal plane. However, the present invention is not limited to this. The front panel 13 may be a flat surface extending horizontally.

As described above, a cover for a blood pressure meter capable of accommodating a cuff belt of the present disclosure includes: a main body of a blood pressure meter having a bottom surface placed on a support surface, a front panel extending so that its height gradually increases from the front toward the rear or extending horizontally, and a back surface extending in a height direction by connecting a rear edge portion of the bottom surface and a rear edge portion of the front panel, the cover for a blood pressure meter having a belt-like outer shape extending from one end to another end along a longitudinal direction, the cover for a blood pressure meter comprising:
 a coupling region provided on the one end side in the longitudinal direction and detachably attached to the bottom surface of the main body;
 a tray region connected to a side of the coupling region opposite to the one end, disposed so as to face the back surface of the main body, and receiving the accommodated cuff belt;
 a panel cover region provided on the other end side in the longitudinal direction and capable of covering the front panel of the main body; and
 a storage cover region connecting the tray region and the panel cover region, wherein
 in a cover-coupled state where the coupling region is detachably attached to the bottom surface of the main body, the panel cover region and the storage cover region are configured to be openable and closable with respect to the front panel and the tray region.

In this specification, the "main body" of the blood pressure meter refers to a casing and includes at least a bottom surface, a front panel, and a back surface. Typically, the front panel is provided with an operation portion for a user to instruct on/off of blood pressure measurement, and a display that displays information on blood pressure.

Additionally, the "support surface" typically refers to a horizontal surface such as a desk, a table, or a floor. Note, however, that the support surface may be slightly inclined with respect to a horizontal plane.

Additionally, the panel cover region and the storage cover region capable of being "opened" with respect to the front panel and the tray region means that the panel cover region and the storage cover region can be separated from the front panel and the tray region, and the front panel and the tray region can become accessible by the user. The panel cover region and the storage cover region capable of being "closed" with respect to the front panel and the tray region means that the panel cover region and the storage cover region can come close to the front panel and the tray region, and cover the front panel and the tray region.

The cover for a blood pressure meter according to the invention has a belt-like outer shape extending from one end to the other end along the longitudinal direction, and has a coupling region that is detachably attached to the bottom surface of the main body of the blood pressure meter on the one end side in the longitudinal direction. When attaching the cover for a blood pressure meter, the user detachably attaches the coupling region to the bottom surface of the main body (this is referred to as a "cover-coupled state"). In the cover-coupled state, a tray region that is connected to the side of the coupling region opposite to the one end is disposed so as to face the back surface of the main body. Additionally, the panel cover region and the storage cover region are configured to be openable and closable with respect to the front panel and the tray region in the cover-coupled state.

Here, when the panel cover region and the storage cover region are opened with respect to the front panel and the tray region, the panel cover region and the storage cover region are separated from the front panel and the tray region, and the front panel and the tray region become accessible by the user. For example, when an operation portion is provided on the front panel, the user can operate the operation portion to instruct on/off of blood pressure measurement. Additionally, when a display is provided on the front panel, the user can see information related to blood pressure (e.g., blood pressure value obtained as a measurement result) by looking at the display. Additionally, when the blood pressure measurement is completed, for example, the user can place a cuff belt rolled into a roll shape, for example, in a space where the back surface of the main body and the tray region face each other. As a result, the placed cuff belt is received by the back surface of the main body and the tray region. Additionally, when starting blood pressure measurement, the user can take out the cuff belt from the space where the back surface of the main body and the tray region face each other in the reverse direction.

When the panel cover region and the storage cover region are closed with respect to the front panel and the tray region, the panel cover region and the storage cover region come close to the front panel and the tray region, respectively, and cover the front panel and the tray region. Thus, the main body is covered and protected by the cover for a blood pressure meter. Additionally, when the cuff belt (e.g., rolled into a roll shape) is placed in a space where the back surface of the main body and the tray region face each other, the cuff belt is surrounded and held by the back surface of the main body, the tray region, and the storage cover region. That is, the back surface of the main body, the tray region, and the storage cover region form a space (referred to as a "cuff belt storage portion") that surrounds the cuff belt, and the cuff belt storage portion accommodates the cuff belt.

On the other hand, when removing the cover for a blood pressure meter, the user removes the coupling region from the bottom surface of the main body. As a result, the cover for a blood pressure meter is not attached to the main body (this is referred to as a "cover non-coupled state"). In the cover non-coupled state, the blood pressure meter does not become bulky because of the cover for a blood pressure meter.

In the cover for a blood pressure meter according to one embodiment, a first boundary portion connecting the tray region and the storage cover region and/or a second boundary portion connecting the storage cover region and the panel cover region are foldable.

Here, "foldable" means that the portion is soft enough to bend by the weight of the cover for a blood pressure meter without the user applying force, for example. For example, the belt-like outer shape is configured of an inner cloth facing the main body, an outer cloth facing the inner cloth, and a plate-like core material sandwiched between the inner cloth and the outer cloth along the longitudinal direction. Then, at the first and second boundary portions, a gap is formed between the core member forming the tray region and the core member forming the storage cover region, and/or between the core member forming the storage cover region and the core member forming the panel cover region in the longitudinal direction. As a result, the first and second boundary portions are formed only of the inner cloth and the outer cloth, and are configured to be soft enough to bend by the weight of the cover for a blood pressure meter.

In the cover for a blood pressure meter according to the embodiment, since the first boundary portion connecting the tray region and the storage cover region and/or the second boundary portion connecting the storage cover region and the panel cover region are foldable, when the panel cover region and the storage cover region are opened with respect to the front panel and the tray region, the panel cover region and the storage cover region do not maintain the raised state, and are laid down by their own weight. Hence, when viewed by the user from the back surface side of the main body, a problem that the display (provided on the front panel of the main body) is hidden by the cover and is difficult to see does not occur. Additionally, when the user opens and closes the panel cover region and the storage cover region with respect to the front panel and the tray region, it is not necessary to apply a strong force to the panel cover region and the storage cover region. Hence, the first boundary portion connecting the tray region and the storage cover region and/or the second boundary portion connecting the storage cover region and the panel cover region are less likely to break.

In the cover for a blood pressure meter according to one embodiment, the coupling region has a second hook-and-loop fastener capable of detachably engaging with a first hook-and-loop fastener provided on the bottom surface of the main body, and the coupling region is detachably attached to the bottom surface of the main body by detachably engaging the second hook-and-loop fastener with the first hook-and-loop fastener.

Here, for example, the "first hook-and-loop fastener" is configured by providing any of multiple visually minute loops or multiple visually minute hooks in a standing manner on a planar base material. The "second hook-and-loop fastener" is configured by providing the other of the multiple loops and the multiple hooks in a standing manner on a planar base material.

In the cover for a blood pressure meter according to the embodiment, the coupling region has a second hook-and-loop fastener that can be detachably engaged with a first hook-and-loop fastener provided on the bottom surface of the main body. The coupling region is detachably attached to the bottom surface of the main body by detachably engaging the second hook-and-loop fastener with the first hook-and-loop fastener. Accordingly, the coupling region is easily attached to the bottom surface of the main body, and conversely, the coupling region is easily detached from the bottom surface of the main body.

In the cover for a blood pressure meter according to one embodiment, the coupling region has a hook to be engaged or a projection to be closely fitted with a receiving hole provided in the bottom surface of the main body, and the coupling region is detachably attached to the bottom surface of the main body by engaging the hook or closely fitting the projection with the receiving hole.

In the cover for a blood pressure meter of the embodiment, the coupling region has a hook to be engaged or a projection to be closely fitted with a receiving hole provided in the bottom surface of the main body. The coupling region is detachably attached to the bottom surface of the main body by engaging the hook or closely fitting the projection with the receiving hole. Accordingly, the coupling region is easily attached to the bottom surface of the main body, and conversely, the coupling region is easily detached from the bottom surface of the main body.

In the cover for a blood pressure meter according to one embodiment, the panel cover region has a second undulation element having a shape to be fitted to a protruding or recessed first undulation element formed on the front panel of the main body in a position corresponding to the first undulation element, and the panel cover region is aligned with the front panel of the main body by fitting the second undulation element to the first undulation element.

In the cover for a blood pressure meter according to the embodiment, the panel cover region has a second undulation element having a shape to be fitted to a protruding or recessed first undulation element formed on the front panel of the main body in a position corresponding to the first undulation element. Thus, when the panel cover region and the storage cover region are closed with respect to the front panel and the tray region, for example, the panel cover region is aligned with the front panel of the main body by fitting the second undulation element to the first undulation element. Hence, it is possible to prevent a situation in which the panel cover region is displaced relative to the front panel of the main body in a transverse direction or a longitudinal direction when viewed from the front, for example. Accordingly, the appearance is improved.

In the cover for a blood pressure meter according to one embodiment, the panel cover region has a second magnetic element that attracts and is attracted by a first magnetic element incorporated in the front panel or the back surface of the main body by magnetic force in a position corresponding to the first magnetic element, and the panel cover region is aligned with the front panel of the main body by attraction between the second magnetic element and the first magnetic element by magnetic force.

Here, as the combination of a "first magnetic element" and a "second magnetic element" that are attracted to each other by magnetic force, a combination of a magnet and a magnet, or a combination of a magnet and a magnetic material (e.g., iron piece) can be adopted, for example.

In the cover for a blood pressure meter according to the embodiment, the panel cover region has a second magnetic element that attracts and is attracted by a first magnetic element incorporated in the front panel or the back surface of the main body by magnetic force in a position corresponding to the first magnetic element. Thus, when the panel cover region and the storage cover region are closed with respect to the front panel and the tray region, for example, the panel cover region is aligned with the front panel of the main body by the attraction between the second magnetic element and the first magnetic element by magnetic force. Hence, it is possible to prevent a situation in which the panel cover region is displaced relative to the front panel of the main body in a transverse direction or a longitudinal direction when viewed from the front, for example. Accordingly, the appearance is improved.

In the cover for a blood pressure meter according to one embodiment, the panel cover region is configured to be foldable or flexible at a plurality of locations in the longitudinal direction.

In the cover for a blood pressure meter according to the embodiment, the panel cover region is configured to be foldable or flexible at multiple locations in the longitudinal direction. As a result, when the panel cover region is opened with respect to the front panel in the cover-coupled state while the storage cover region covers the tray region, the panel cover region is folded or flexed at multiple locations in the longitudinal direction. Accordingly, the user can open the panel cover region easily with a smaller hand movement than when the panel cover region remains flat. The opened panel cover region maintains a relatively small posture by its own weight.

In the cover for a blood pressure meter according to one embodiment, the storage cover region is configured to be foldable or flexible at a plurality of locations in the longitudinal direction.

In the cover for a blood pressure meter according to the embodiment, the storage cover region is configured to be foldable or flexible at multiple locations in the longitudinal direction. As a result, when the storage cover region is opened with respect to the tray region in the cover-coupled state, the panel cover region is folded or flexed at multiple locations in the longitudinal direction. Accordingly, the user can open the storage cover region easily.

In the cover for a blood pressure meter according to one embodiment, in the cover-coupled state, the tray region maintains a shape curving so as to protrude downward and extending obliquely upward from a rear edge portion of the bottom surface of the main body.

In the cover for a blood pressure meter according to the embodiment, in the cover-coupled state, the tray region maintains a shape curving so as to protrude downward and extending obliquely upward from a rear edge portion of the bottom surface of the main body. Accordingly, the tray region is suitable for receiving a cuff belt rolled into a roll shape.

In the cover for a blood pressure meter according to one embodiment, a height of an upper end of the tray region in the cover-coupled state is set within a range of an angle of depression of 45 degrees to an angle of elevation of 25 degrees when viewed from a center line of a cuff belt rolled into a roll shape and received in the tray region.

Here, the "upper end" of the tray region in the cover-coupled state refers to a boundary portion (first boundary portion) between the tray region and the storage cover region.

In the cover for a blood pressure meter according to the embodiment, the height of the upper end of the tray region in the cover-coupled state is set higher than an angle of depression of 45 degrees when viewed from the center line of the cuff belt rolled into a roll shape and received in the tray region. Hence, even when the panel cover region and the storage cover region are opened with respect to the front panel and the tray region and laid down, the upper end of the tray region prevents the cuff belt from falling backward from the tray region. On the other hand, the height of the upper end of the tray region in the cover-coupled state is set to be lower than an angle of elevation of 25 degrees when viewed from the center line of the cuff belt rolled into a roll shape and received in the tray region. Hence, when the panel cover region and the storage cover region are opened with respect to the front panel and the tray region, the cuff belt rolled into a roll shape can be easily placed in or removed from the space where the back surface of the main body and the tray region face each other.

In the cover for a blood pressure meter according to one embodiment, stopper elements are provided in both edge portions of the tray region to prevent the cuff belt received in the tray region from jumping out to the side.

Here, the "both edge portions" of the tray region refer to portions corresponding to both ends in the width direction perpendicular to the longitudinal direction of the cover for a blood pressure meter.

In the cover for a blood pressure meter according to the embodiment, stopper elements are provided at both edge portions of the tray region to prevent the cuff belt received in the tray region from jumping out to the side. Hence, for example, in a state where the cuff belt is placed in the space where the back surface of the main body and the tray region face each other, it is possible to prevent the cuff belt from needlessly jumping out to the side.

In another aspect, the blood pressure meter of the present disclosure comprises a removable cover for a blood pressure meter capable of accommodating a cuff belt, wherein:

a main body of the blood pressure meter has a bottom surface placed on a support surface, a front panel extending so that its height gradually increases from the front toward the rear or extending horizontally, and a back surface extending in a height direction by connecting a rear edge portion of the bottom surface and a rear edge portion of the front panel;

the cover for a blood pressure meter has a belt-like outer shape extending from one end to another end along a longitudinal direction, and includes a coupling region provided on the one end side in the longitudinal direction and detachably attached to the bottom surface of the main body, a tray region connected to a side of the coupling region opposite to the one end, facing the back surface of the main body, and receiving the accommodated cuff belt, a panel cover region provided on the other end side in the longitudinal direction and capable of covering the front panel of the main body, and a storage cover region connecting the tray region and the panel cover region; and in a cover-coupled state where the coupling region is detachably attached to the bottom surface of the main body, the panel cover region and the storage cover region are configured to be openable and closable with respect to the front panel and the tray region.

In the blood pressure meter according to the disclosure, the cover for a blood pressure meter has a belt-like outer shape extending from one end to the other end along the longitudinal direction, and has a coupling region that is detachably attached to a bottom surface of a main body of the blood pressure meter on the one end side in the longitudinal direction. When attaching the cover for a blood pressure meter, the user detachably attaches the coupling region to the bottom surface of the main body (cover-coupled state). In the cover-coupled state, a tray region that is connected to the side of the coupling region opposite to the one end is disposed so as to face the back surface of the main body. Additionally, the panel cover region and the storage cover region are configured to be openable and closable with respect to the front panel and the tray region in the cover-coupled state.

Here, when the panel cover region and the storage cover region are opened with respect to the front panel and the tray region, the panel cover region and the storage cover region are separated from the front panel and the tray region, and the front panel and the tray region become accessible by the user. For example, when an operation portion is provided on the front panel, the user can operate the operation portion to instruct on/off of blood pressure measurement. Additionally, when a display is provided on the front panel, the user can see information related to blood pressure (e.g., blood pressure value obtained as a measurement result) by looking at the display. Additionally, when the blood pressure measurement is completed, for example, the user can place a cuff belt rolled into a roll shape, for example, in a space where the back surface of the main body and the tray region face each other. As a result, the placed cuff belt is received by the back surface of the main body and the tray region.

When the panel cover region and the storage cover region are closed with respect to the front panel and the tray region, the panel cover region and the storage cover region come close to the front panel and the tray region and cover the front panel and the tray region. Thus, the main body is covered and protected by the cover for a blood pressure meter. Additionally, when the cuff belt (e.g., rolled into a roll shape) is placed in a space where the back surface of the main body and the tray region face each other, the cuff belt is surrounded and held by the back surface of the main body, the tray region, and the storage cover region. That is, the back surface of the main body, the tray region, and the storage cover region form a cuff belt storage portion, and the cuff belt storage portion accommodates the cuff belt.

On the other hand, when removing the cover for a blood pressure meter, the user removes the coupling region from the bottom surface of the main body. As a result, the cover for a blood pressure meter is not attached to the main body (cover non-coupled state). In this cover non-coupled state, the user can use the blood pressure meter in a small size.

In the blood pressure meter according to one embodiment, the main body has a battery passage opening formed on the bottom surface, and a first battery lid having a shape that is detachably fitted to the battery passage opening;

the cover for a blood pressure meter has a second battery lid being provided integrally with the coupling region and having a shape that is detachably fitted to the battery passage opening; and the cover for a blood pressure meter is attached to the main body by fitting the second battery lid in place of the first battery lid to close the battery passage opening.

Here, the "battery passage opening" refers to an opening for putting a battery into the battery storage portion from the outside of the main body or taking the battery out when the main body incorporates a battery storage portion that accommodates a battery.

In the blood pressure meter according to the embodiment, in the cover non-coupled state, the first battery lid is fitted to the battery passage opening formed on the bottom surface to close the battery passage opening. At this time, the blood pressure meter does not become bulky because of the cover for a blood pressure meter. On the other hand, when attaching the cover for a blood pressure meter, the second battery lid is fitted in place of the first battery lid to close the battery passage opening, whereby the cover for a blood pressure meter is attached to the main body. As a result, the coupling region of the cover for a blood pressure meter is easily attached to and detached from the bottom surface of the main body.

In still another aspect, the disclosure is not limited to a blood pressure meter, but relates to a technique for detachably attaching a cover for covering an outer surface of a main body to the main body of a general device.

A device of the disclosure is
a device including a main body and a cover for covering an outer surface of the main body, in which:
the main body has a first battery lid having a shape that is detachably fitted to a battery passage opening formed on the outer surface;
the cover has an outer surface cover portion covering the outer surface of the device, and a second battery lid provided integrally with the outer surface cover portion and having a shape that is detachably fitted to the battery passage opening; and
when attaching the cover, the second battery lid is fitted in place of the first battery lid to close the battery passage opening.

In the device according to the disclosure, in the cover non-coupled state, the first battery lid is fitted to the battery passage opening to close the battery passage opening formed on the outer surface. At this time, the device does not become bulky because of the cover. Hence, the device can be used in a small size. On the other hand, when attaching the cover, the second battery lid is fitted in place of the first battery lid to close the battery passage opening. As a result, the cover-coupled state is formed, and the outer surface of the main body is covered and protected by the outer surface cover portion of the cover.

The above embodiments are illustrative, and various modifications can be made without departing from the scope of the present invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A cover for a blood pressure meter capable of accommodating a cuff belt,
a main body of a blood pressure meter having a bottom surface placed on a support surface, a front panel extending so that its height gradually increases from the front toward the rear or extending horizontally, and a back surface extending in a height direction by connecting a rear edge portion of the bottom surface and a rear edge portion of the front panel, the cover for a blood pressure meter having a belt-like outer shape extending from one end to another end along a longitudinal direction,
the cover for a blood pressure meter comprising:
a coupling region provided on the one end side in the longitudinal direction and configured to be detachably attached to the bottom surface of the main body;
a tray region connected to a side of the coupling region opposite to the one end, disposed so as to face the back surface of the main body, and configured to receive the cuff belt to be accommodated;
a panel cover region provided on the other end side in the longitudinal direction and configured to be capable of covering the front panel of the main body; and
a storage cover region connecting the tray region and the panel cover region, wherein
in a cover-coupled state where the coupling region of the cover is detachably attached to the bottom surface of the main body of the blood pressure meter, the panel cover region and the storage cover region are configured to be openable and closable with respect to the front panel and the tray region.

2. The cover for a blood pressure meter according to claim 1, wherein
a first boundary portion connecting the tray region and the storage cover region and/or a second boundary portion connecting the storage cover region and the panel cover region are foldable.

3. The cover for a blood pressure meter according to claim 1, wherein
the coupling region has a second hook-and-loop fastener configured to be capable of detachably engaging with a first hook-and-loop fastener provided on the bottom surface of the main body, and
the coupling region is detachably attached to the bottom surface of the main body by detachably engaging the second hook-and-loop fastener with the first hook-and-loop fastener.

4. The cover for a blood pressure meter according to claim 1, wherein
the coupling region has a hook to be engaged or a projection configured to be closely fitted with a receiving hole provided in the bottom surface of the main body, and
the coupling region is detachably attached to the bottom surface of the main body by engaging the hook or closely fitting the projection with the receiving hole.

5. The cover for a blood pressure meter according to claim 1, wherein
the panel cover region has a second undulation element having a shape to be fitted to a protruding or recessed first undulation element formed on the front panel of the main body in a position corresponding to the first undulation element, and
the panel cover region is aligned with the front panel of the main body by fitting the second undulation element to the first undulation element.

6. The cover for a blood pressure meter according to claim 1, wherein
the panel cover region has a second magnetic element configured to attract and be attracted by a first magnetic element incorporated in the front panel or the back surface of the main body by magnetic force in a position corresponding to the first magnetic element, and the panel cover region is aligned with the front panel of the main body by attraction between the second magnetic element and the first magnetic element by magnetic force.

7. The cover for a blood pressure meter according to claim 1, wherein
the panel cover region is configured to be foldable or flexible at a plurality of locations in the longitudinal direction.

8. The cover for a blood pressure meter according to claim 1, wherein
the storage cover region is configured to be foldable or flexible at a plurality of locations in the longitudinal direction.

9. The cover for a blood pressure meter according to claim 1, wherein
in the cover-coupled state, the tray region maintains a shape curving so as to protrude downward and extending obliquely upward from a rear edge portion of the bottom surface of the main body.

10. The cover for a blood pressure meter according to claim 9, wherein
a height of an upper end of the tray region in the cover-coupled state is set within a range of an angle of depression of 45 degrees to an angle of elevation of 25 degrees when viewed from a center line of a cuff belt rolled into a roll shape and received in the tray region.

11. The cover for a blood pressure meter according to claim 1, wherein
stopper elements are provided in both edge portions of the tray region and are configured to prevent the cuff belt received in the tray region from jumping out to the side.

12. A blood pressure meter comprising:
a removable cover for a blood pressure meter capable of accommodating a cuff belt; and
a main body of the blood pressure meter having a bottom surface placed on a support surface, a front panel extending so that its height gradually increases from the front toward the rear or extending horizontally, and a back surface extending in a height direction by connecting a rear edge portion of the bottom surface and a rear edge portion of the front panel, wherein:
the cover for a blood pressure meter has a belt-like outer shape extending from one end to another end along a longitudinal direction, and includes a coupling region provided on the one end side in the longitudinal direction and configured to be detachably attached to the bottom surface of the main body,
a tray region connected to a side of the coupling region opposite to the one end, facing the back surface of the main body, and configured to receive the cuff belt to be accommodated,
a panel cover region provided on the other end side in the longitudinal direction and configured to be capable of covering the front panel of the main body, and
a storage cover region connecting the tray region and the panel cover region; and
in a cover-coupled state where the coupling region of the cover is detachably attached to the bottom surface of the main body of the blood pressure meter, the panel cover region and the storage cover region are configured to be openable and closable with respect to the front panel and the tray region.

13. The blood pressure meter according to claim 12, wherein:
the main body has a battery passage opening formed on the bottom surface, and a first battery lid having a shape that is detachably fitted to the battery passage opening;
the cover for a blood pressure meter has a second battery lid being provided integrally with the coupling region and having a shape that is detachably fitted to the battery passage opening; and
the cover for a blood pressure meter is attached to the main body by fitting the second battery lid in place of the first battery lid to close the battery passage opening.

* * * * *